(12) United States Patent
Goldstein et al.

(10) Patent No.: US 8,194,864 B2
(45) Date of Patent: Jun. 5, 2012

(54) EARHEALTH MONITORING SYSTEM AND METHOD I

(75) Inventors: Steven W. Goldstein, Delray Beach, FL (US); John Usher, Montreal (CA); Brian Fligor, Mansfield, MA (US); John P. Keady, Boca Raton, FL (US)

(73) Assignee: Personics Holdings Inc., Boca Raton, FL (US)

( * ) Notice: Subject to any disclaimer, the term of this patent is extended or adjusted under 35 U.S.C. 154(b) by 1174 days.

(21) Appl. No.: 11/928,290

(22) Filed: Oct. 30, 2007

(65) Prior Publication Data
US 2008/0212787 A1 Sep. 4, 2008

Related U.S. Application Data

(63) Continuation-in-part of application No. 11/757,152, filed on Jun. 1, 2007.

(60) Provisional application No. 60/803,708, filed on Jun. 1, 2006.

(51) Int. Cl.
*H04R 29/00* (2006.01)
*A61F 11/06* (2006.01)
*A61B 5/12* (2006.01)

(52) U.S. Cl. .............. 381/56; 381/58; 381/72; 73/585

(58) Field of Classification Search .............. 381/56–60, 381/72; 600/25; 73/585, 645, 646
See application file for complete search history.

(56) References Cited

U.S. PATENT DOCUMENTS

| | | | |
|---|---|---|---|
| 3,802,535 A | 4/1974 | Peake | |
| 3,987,245 A | 10/1976 | Fasen | |
| 4,554,639 A | 11/1985 | Baker | |
| 4,947,432 A | 8/1990 | Topholm | |
| 5,430,826 A | 7/1995 | Webster | |
| 5,692,059 A | 11/1997 | Kruger | |
| 5,757,930 A * | 5/1998 | Seidemann et al. | 381/60 |
| 6,379,314 B1 | 4/2002 | Horn | |
| 6,456,199 B1 * | 9/2002 | Michael | 340/573.1 |
| 6,473,512 B1 | 10/2002 | Juneau | |
| 6,648,820 B1 | 11/2003 | Sarel | |
| 6,754,359 B1 * | 6/2004 | Svean et al. | 381/328 |
| 6,826,515 B2 * | 11/2004 | Bernardi et al. | 702/191 |
| 6,840,908 B2 | 1/2005 | Edwards | |
| 7,756,281 B2 | 7/2010 | Goldstein | |

(Continued)

FOREIGN PATENT DOCUMENTS
EP 165468 A1 12/1985
(Continued)

OTHER PUBLICATIONS

Osha, "Occupational Noise Exposure", Jul. 1, 2005, Section 1910.95, pp. 211-223.

(Continued)

*Primary Examiner* — Jesse Elbin
(74) *Attorney, Agent, or Firm* — RatnerPrestia

(57) ABSTRACT

Methods of operating an audio device are provided. A method includes calculating estimated sound pressure levels (SPLs) for drive signals directed to an ear canal receiver (ECR) during a time increment $\Delta t$; calculating an estimated SPL_Dose during the time increment $\Delta t$ using the estimated sound pressure levels; and calculating a total SPL_Dose at a time t of the audio device using the estimated SPL_Dose.

5 Claims, 22 Drawing Sheets

U.S. PATENT DOCUMENTS

| | | |
|---|---|---|
| 2003/0165246 A1 | 9/2003 | Kvaloy |
| 2005/0020873 A1 | 1/2005 | Berrang |
| 2005/0117765 A1 | 6/2005 | Meyer |
| 2005/0250439 A1 | 11/2005 | Leslie |
| 2005/0254665 A1 | 11/2005 | Vaudrey |
| 2005/0254667 A1 | 11/2005 | Michael |
| 2006/0137934 A1* | 6/2006 | Kurth ............................ 181/135 |
| 2007/0129828 A1 | 6/2007 | Lee |
| 2007/0147624 A1 | 6/2007 | Fischer |
| 2007/0270988 A1 | 11/2007 | Goldstein |
| 2008/0194984 A1 | 8/2008 | Keefe |

FOREIGN PATENT DOCUMENTS

| | | |
|---|---|---|
| EP | 1615468 | 1/2006 |
| WO | 2006002055 | 1/2006 |

OTHER PUBLICATIONS

Office Action for U.S. Appl. No. 11/931,252, mailed Jul. 19, 2011.

* cited by examiner

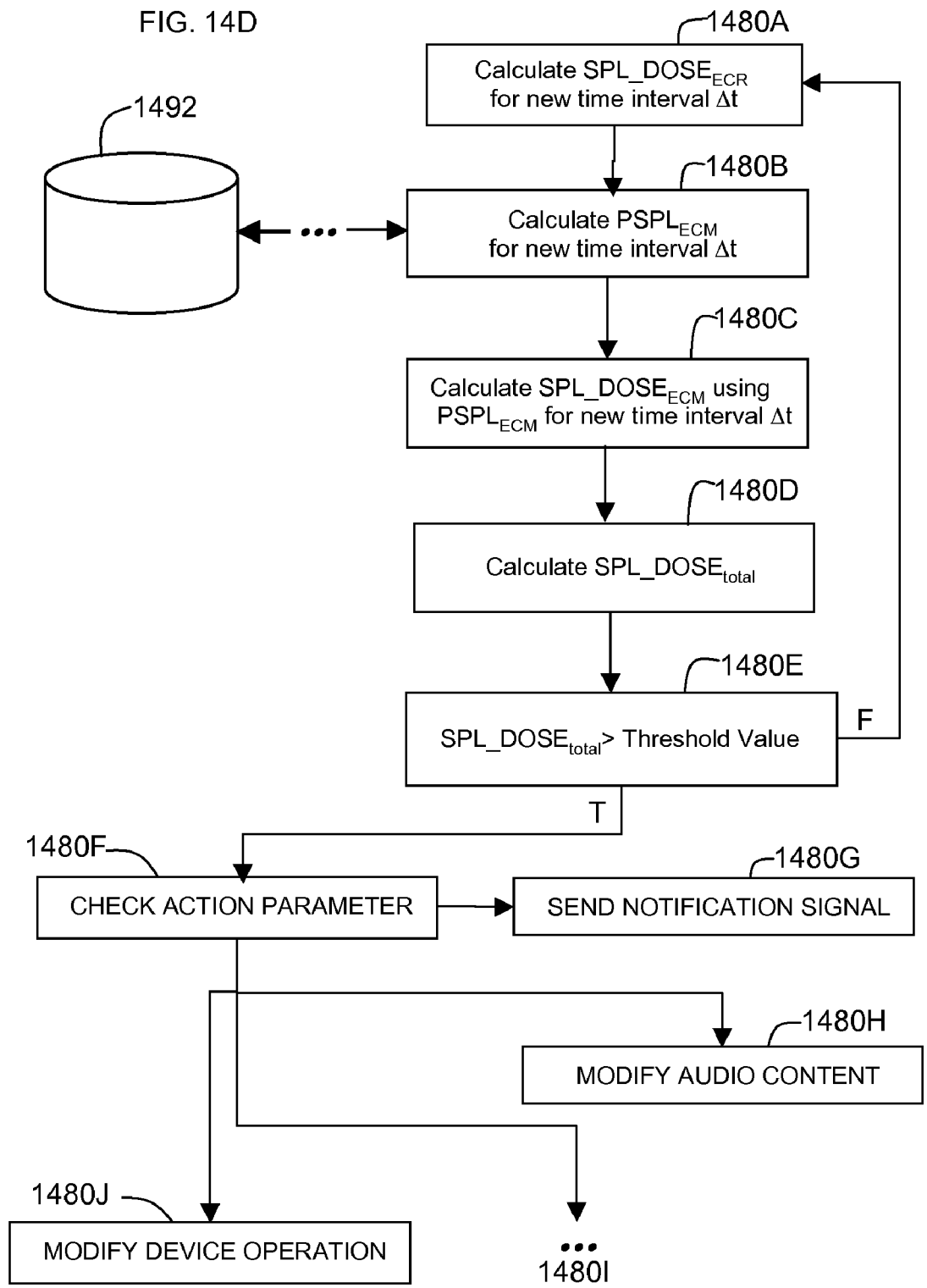

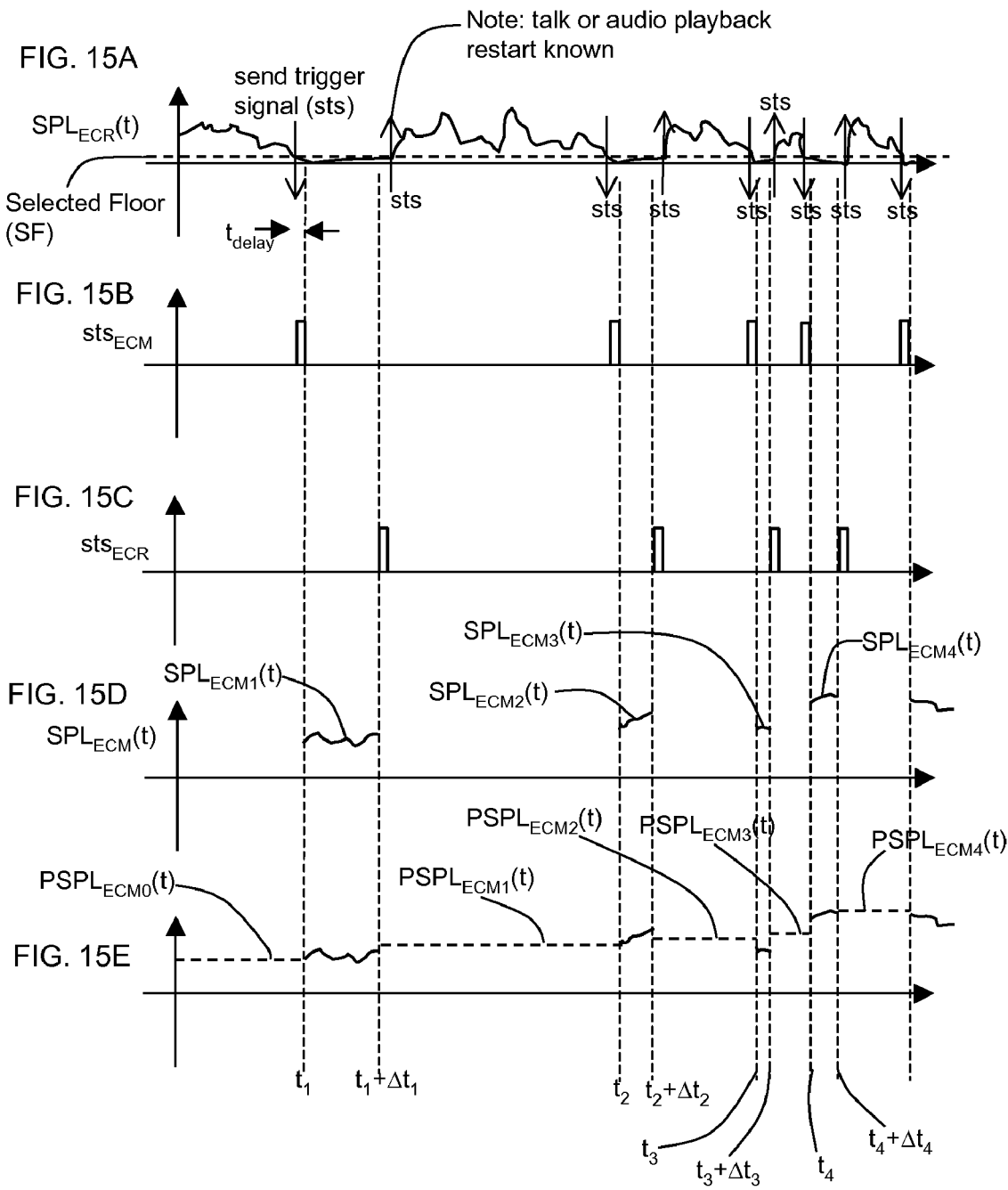

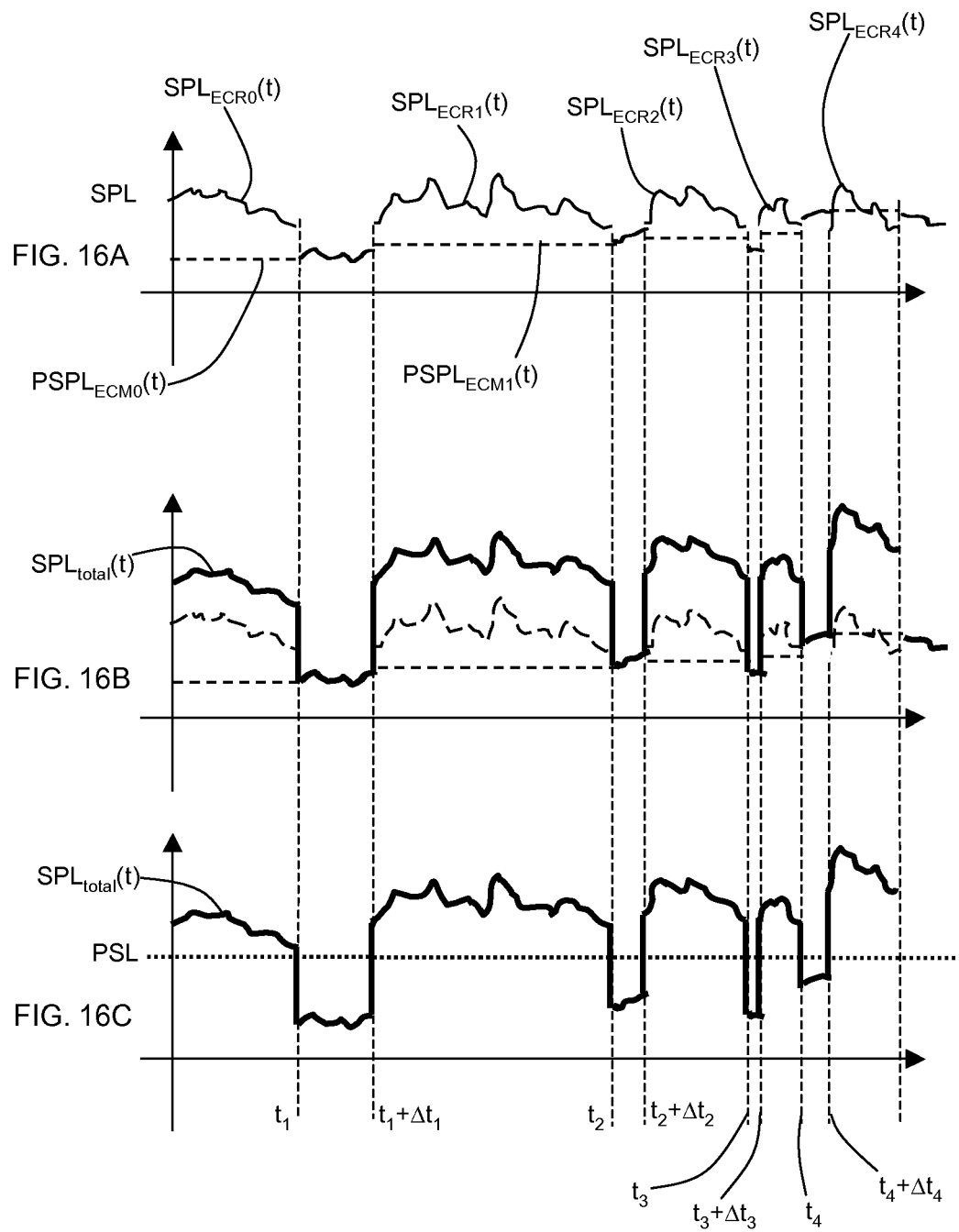

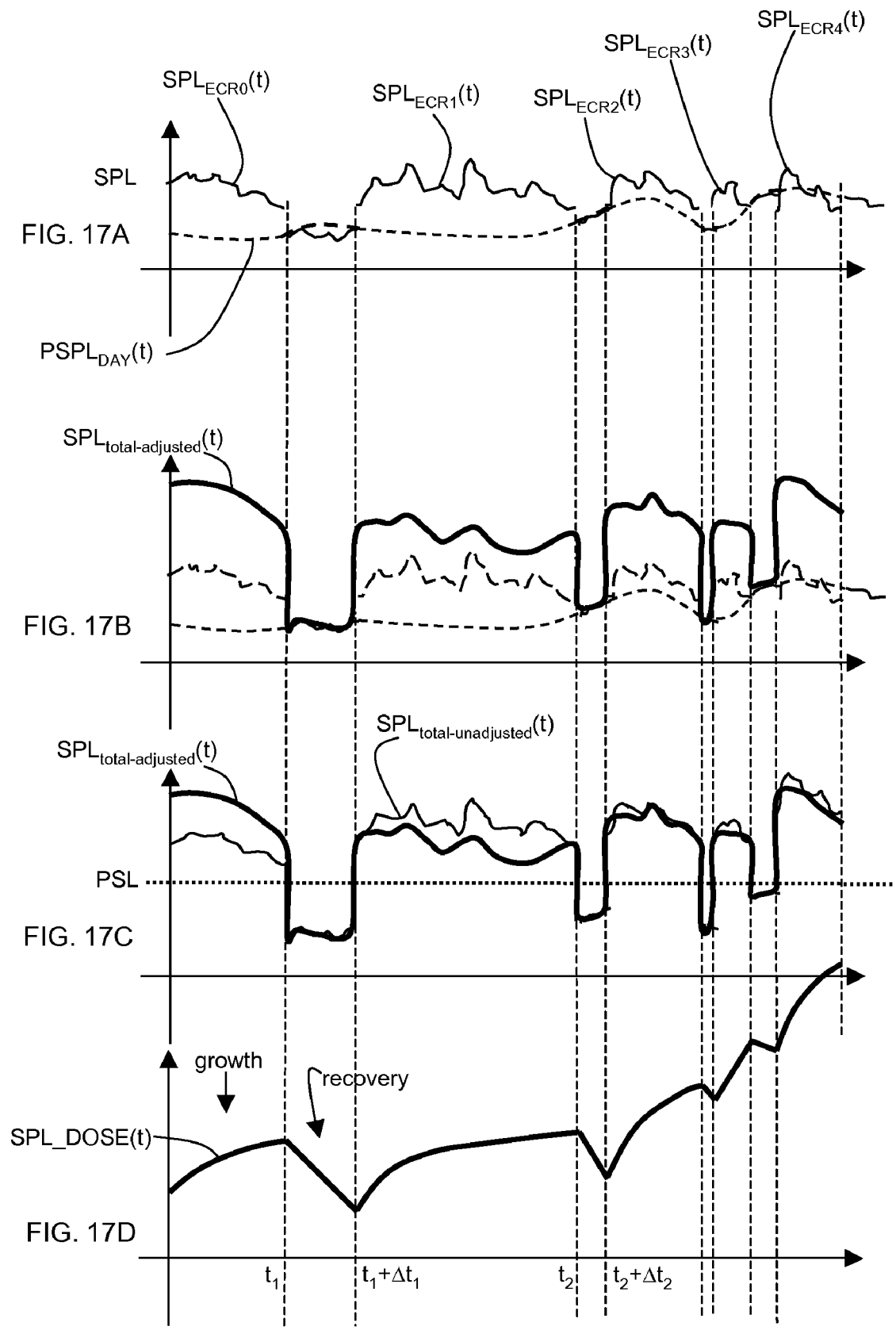

EARHEALTH MONITORING SYSTEM AND METHOD I

This application is a Continuation-in-Part of U.S. patent application Ser. No. 11/757,152 filed on 1 Jun. 2007, the disclosure of which is incorporated herein by reference in its entirety, which in turn claims priority from U.S. Provisional Application No. 60/803,708 filed 1 Jun. 2006.

FIELD OF THE INVENTION

The present invention relates to a device that monitors acoustic energy directed to an ear, and more particularly, though not exclusively, to an earpiece that monitors acoustic sound pressure level dose received by a user's ear.

BACKGROUND OF THE INVENTION

With the advent of an industrial society, people are exposed to noise pollution at greater and greater levels; both from background, such as street traffic, airplanes, construction sites and intentional exposure to high sound levels such as cell phones, MP3 players, and rock concerts. Studies show that ear damage, leading to permanent hearing impairment is not only increasing in the general population, but increasing at a significantly faster rate in younger populations.

The potential for hearing damage is a function of both the level and the duration of exposure to the sound stimulus. Safe listening durations at various loudness levels are known, and can be calculated by averaging audio output levels over time to yield a time-weighted average. Standard damage-risk guidelines published by OSHA, NIOSH or other agencies are known. This calculation can be even further improved by accounting for aspects of the playback scenario, specifically the characteristics of the sound source and their proximity to the listener's ear.

Studies have also indicated that hearing damage is a cumulative phenomenon. Although hearing damage due to industrial or background noise exposure is more thoroughly understood, the risk of exposing one's self to excessive noise, especially with the use of headphones has also been recently studied. Protecting the ear from ambient noise is primarily done with the use of static earplugs that attempt to shield the inner ear from excessively high decibel noise. Background noise canceling earphones such as those produced by Bose and others, attempt to protect the ear from excessive ambient noise by producing a counter noise wave to cancel out the ambient noise at the ear. These prior art devices have been less than satisfactory because they do not completely prevent high decibel noise from reaching the ear, and do not account for the duration of exposure to harmful sounds at the ear.

It is also known from the prior art to provide active noise reduction at the ear to protect the ear from exposure to loud noises as disclosed in U.S. patent Application No. US2005/0254665. The art actively attenuating noise reaching the inner ear utilizing a control; a connection with an earpiece and attenuating the noise to the ear. However, there is no monitoring of the noise over time to account for the cumulative effect. Furthermore, there is no accounting for any restorative effects within the ear for sound level exposures which are sufficiently low to allow recovery, rather than destruction.

Dosimeters, such as that described in U.S. published Application No. US2005/0254667 are known. The device periodically measures prior sound level in the ambient environment. However, the device does not take into account the cumulative effect of the noise over multiple incidences of exposure (e.g., one day to the next) or the effect of any restorative period. Furthermore, no remedial action is automatically taken as a result of the readings.

It is also known from the prior art that headphones for consumer electronics have been provided with a predetermined maximum output level in an attempt to prevent ear damage. This approach is ineffective as it does not take into account listening duration and the calculation of risk for auditory injury. Other headphones are maximum-limited to produce levels that can still result in significant overexposure given enough time, or limit the user to levels, which may not be sufficient to achieve an adequate short term listening level. In the latter case, consumer acceptance for the protective gear could be severely limited and a product would fail to survive in a competitive market and therefore be of no use.

Another alternative known in the art is to reduce the headphone output levels by increasing earphone impedance via an accessory placed between the media player and the earphones. The limitation of this approach is that it gives no consideration to the duration of exposure, and again either the user's chosen listening level cannot be achieved because the maximum level is too limited, or the level is sufficient to allow the user access to high enough sound levels, but risk overexposure due to potential duration of use.

It is known from U.S. Publication No. 2007/0129828 to provide automated control of audio volume parameters in order to protect hearing. A method of operating a media player includes the step of playing back audio media and refining a maximum volume parameter for the playing of the media by the media player. The refining is based at least in part on the playback of audio media during a time period existing prior to the execution of refining the maximum volume allowed. The refinement is intended to minimize harm to the user's hearing.

Applicants cannot confirm that such an approach has been commercialized. However, even if commercialized, it suffers from the shortcomings that the refinement is based on a theoretical noise volume delivered to the ear as a function of the output signal of the device and parameters of the earpiece connected to the device and is based upon a credit system based on volume. There is no measurement of the actual noise delivered to the ear. Furthermore, the calculation does not take into account the ambient noise of the device user nor the noise reduction rate of the earpiece relative to the ambient noise. In other words, the actual volume level to which the ear is exposed is not taken into account. Accordingly, a severe miscalculation of the actual ear exposure, and resulting ear harm, may exist as a result of use of this related art method. Additionally the credit system is not described in detail sufficient for one of ordinary skill to construct the device. For example U.S. Publication No. 2007/0129828 refers to Cal-OSHA profiles, and states in the same paragraph that Cal-OSHA appear to be rudimentary and does not deal with exposure "in a sophisticated way with varying exposure over time" and does not " . . . account for recovery." However, U.S. Publication No. 2007/0129828 states in one example " . . . the maximum allowed volume is determined based upon determined credits with reference to a profile such as profiles provided by . . . (Cal-OSHA) . . . . " However, U.S. Publication No. 2007/0129828, stated that Cal-OSHA doesn't take into effect recovery, and additionally fails to refer to any detailed recovery calculation. Additionally, the credit system is based upon volume, rather than a predicted sound pressure level (PSPL) emitted by a speaker, and thus is an inaccurate predictor of sound pressure level (SPL) experienced by a user's ears due to emissions from the speaker.

Accordingly, a system that overcomes the shortcomings in the related art would be useful.

BRIEF SUMMARY OF THE INVENTION

At least one exemplary embodiment is directed to a method of operating an audio device comprising: calculating estimated sound pressure levels for drive signals directed to an ear canal receiver (ECR) (which can result in an emitted acoustic signal by the ECR) during a time increment $\Delta t$; calculating an estimated SPL_Dose during the time increment $\Delta t$ using the estimated sound pressure levels; and calculating a total SPL_Dose at the time t of the audio device using the estimated SPL_Dose. Additional exemplary embodiments include comparing the estimated sound pressure levels to a permissible sound level (PSL), and if the estimated sound pressure levels are less than PSL within an error margin, then the step of calculating an estimated SPL_Dose uses a recovery function to calculate the updated estimated SPL_Dose during the time increment $\Delta t$.

Additional exemplary embodiments can include: calculating estimated sound pressure levels (SPL1) for drive signals directed to an ear canal receiver (ECR) during a time increment $\Delta t$, when the ECR is in the ECR mode; measuring sound pressure levels (SPL2) for ambient acoustic signals received by the ECR during the time increment $\Delta t$, when the ECR is in the ear canal microphone (ECM) mode; calculating an estimated SPL_Dose during the time increment $\Delta t$ using at least one of SPL1 and SPL2; calculating a total SPL_Dose of the audio device at the time t using the estimated SPL_Dose; and comparing either sound pressure levels SPL1 or SPL2 to a permissible sound level (PSL), and if the used sound pressure levels, SPL1 or SPL2, is less than PSL within an error margin, then the step of calculating an estimated SPL_Dose uses a recovery function to calculate the updated estimated SPL_Dose during the time increment $\Delta t$.

At least one further exemplary embodiment is directed to a method of operating an audio device comprising: calculating estimated sound pressure levels (SPL1) for drive signals directed to an ear canal receiver (ECR) during a time increment $\Delta t$, when the ECR is in the ECR mode; predicting a sound pressure level (PSPL1) for ambient acoustic signals that would be received by the ECR during the time increment $\Delta t$, if the ECR was in the ECM mode but is in ECR mode; calculating an estimated SPL_Dose during the time increment $\Delta t$ using SPL1 and PSPL1; and calculating a total SPL_Dose of the audio device at time t using the estimated SPL_Dose.

At least one exemplary embodiment is directed to a method of operating an audio device comprising: calculating estimated sound pressure levels for drive signals directed to an ear canal receiver (ECR) during a time increment $\Delta t$; calculating an estimated SPL_Dose during the time increment $\Delta t$ using the estimated sound pressure levels; comparing the estimated sound pressure levels to a permissible sound level (PSL), and if the estimated sound pressure levels are less than PSL then the step of calculating an estimated SPL_Dose uses a recovery function that is at least one of a linear function and an exponential function to calculate the estimated SPL_Dose during the time increment $\Delta t$; and calculating a total SPL_Dose of the audio device at the time "t" using the estimated SPL_Dose, where $t=t_0+\Delta t$, where $t_0$ is the time at the beginning of the time increment $\Delta t$.

At least one exemplary embodiment is directed to a method of operating an audio device comprising: calculating estimated sound pressure levels (SPL1) for drive signals directed to an ear canal receiver (ECR) during a time increment $\Delta t$, when the ECR is in the ECR mode; measuring sound pressure levels (SPL2) for ambient acoustic signals received by the ECR during the time increment $\Delta t$, when the ECR is in the ECM mode; predicting a sound pressure level (PSPL1) for ambient acoustic signals that would be received by the ECR during the time increment $\Delta t$, if the ECR was in the ECM mode but is in the ECR mode; calculating an SPL total during the time increment $\Delta t$ using SPL1 and PSPL1 when the ECR is in the ECR mode. If the ECR is in the ECM mode during the time increment $\Delta t$ then SPL total during the time increment $\Delta t$ is calculated using SPL2; calculating an estimated SPL_Dose during the time increment $\Delta t$ using SPL1 and PSPL1 when the ECR is in ECR mode and SPL2 when ECR is in ECM mode; comparing the SPL total to a permissible sound level (PSL), and if SPL total is less than PSL then the step of calculating an updated estimated SPL_Dose uses a recovery function that is at least one of a linear function and an exponential function to calculate the estimated SPL_Dose during the time increment $\Delta t$; and calculating a total SPL_Dose of the audio device at time t using the estimated SPL_Dose, where $t=t_0+\Delta t$, where $t_0$ is the time at the beginning of the time increment $\Delta t$.

Further areas of applicability of exemplary embodiments of the present invention will become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

FIG. 14D illustrates a flow diagram of a method of SPL Dose calculation according to at least one exemplary embodiment;

FIGS. 15A-15E illustrate a method of switching between ECR and ECM modes in accordance with at least one exemplary embodiment;

FIGS. 16A-16C illustrate the formation of SPL total from ECM and ECR values and estimated values (PSPL);

FIGS. 17A-17D illustrate the formulation of an SPL-Dose by a non-limiting example of an optional end of day correction to the previous estimated values (PSPL);

DETAILED DESCRIPTION OF THE INVENTION

Figure 1:
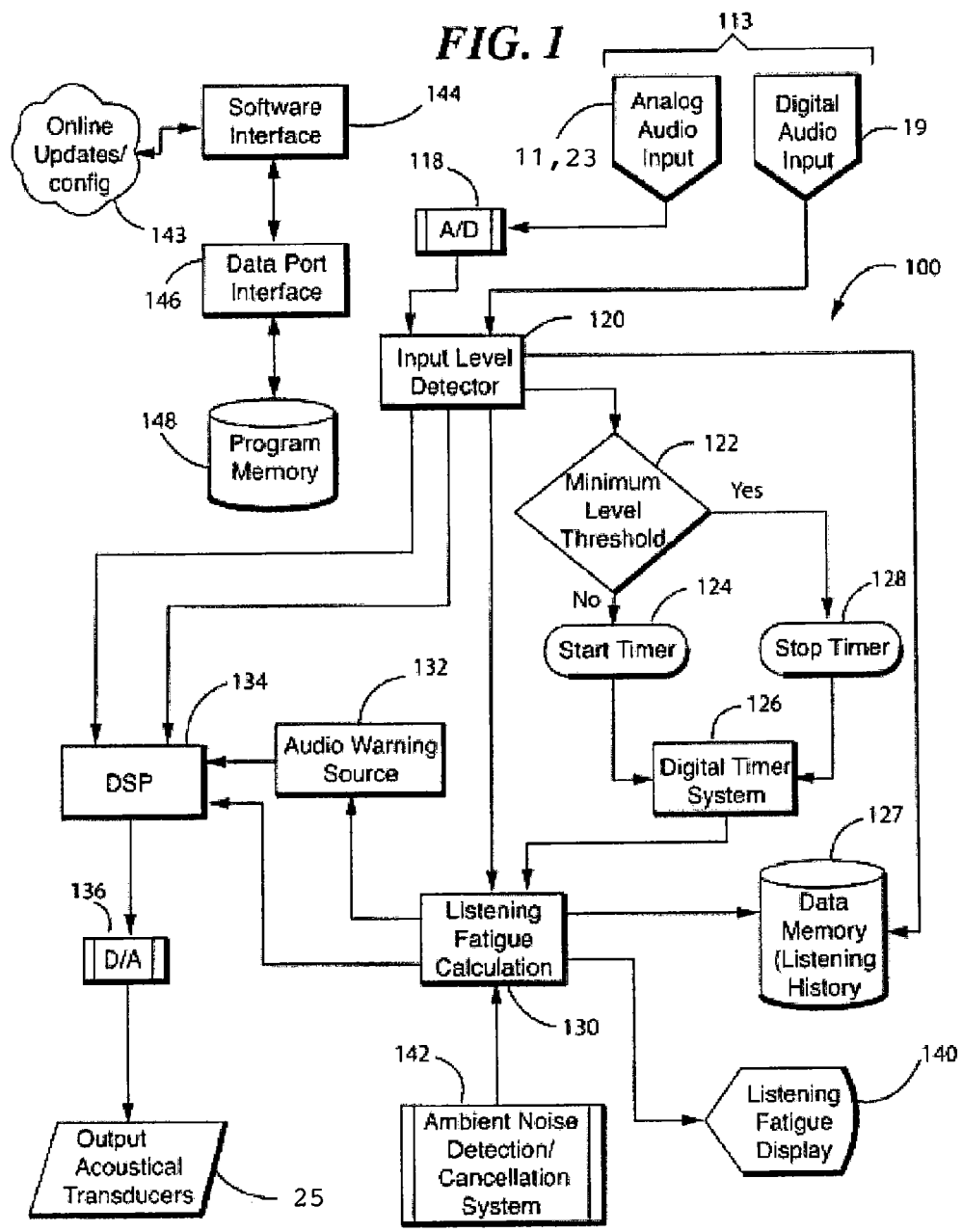
FIG. 1 is a block diagram of the system for measuring and determining exposure to sound over time at the ear constructed in accordance with a first exemplary embodiment of the invention.

The following description of at least one exemplary embodiment is merely illustrative in nature and is in no way intended to limit the invention, its application, or uses.

Processes, techniques, apparatus, and materials as known by one of ordinary skill in the relevant art may not be discussed in detail but are intended to be part of the enabling description where appropriate, for example the fabrication and use of transducers. Additionally in at least one exemplary embodiment the sampling rate of the transducers can be varied to pick up pulses of sound, for example less than 50 milliseconds.

In all of the examples illustrated and discussed herein, any specific values, for example the sound pressure level change, should be interpreted to be illustrative only and non-limiting. Thus, other examples of the exemplary embodiments could have different values.

Note that similar reference numerals and letters refer to similar items in the following figures, and thus once an item is defined in one figure, it may not be discussed for following figures.

Note that herein when referring to correcting or preventing an error or damage (e.g., hearing damage), a reduction of the damage or error and/or a correction of the damage or error are intended.

Figure 2:
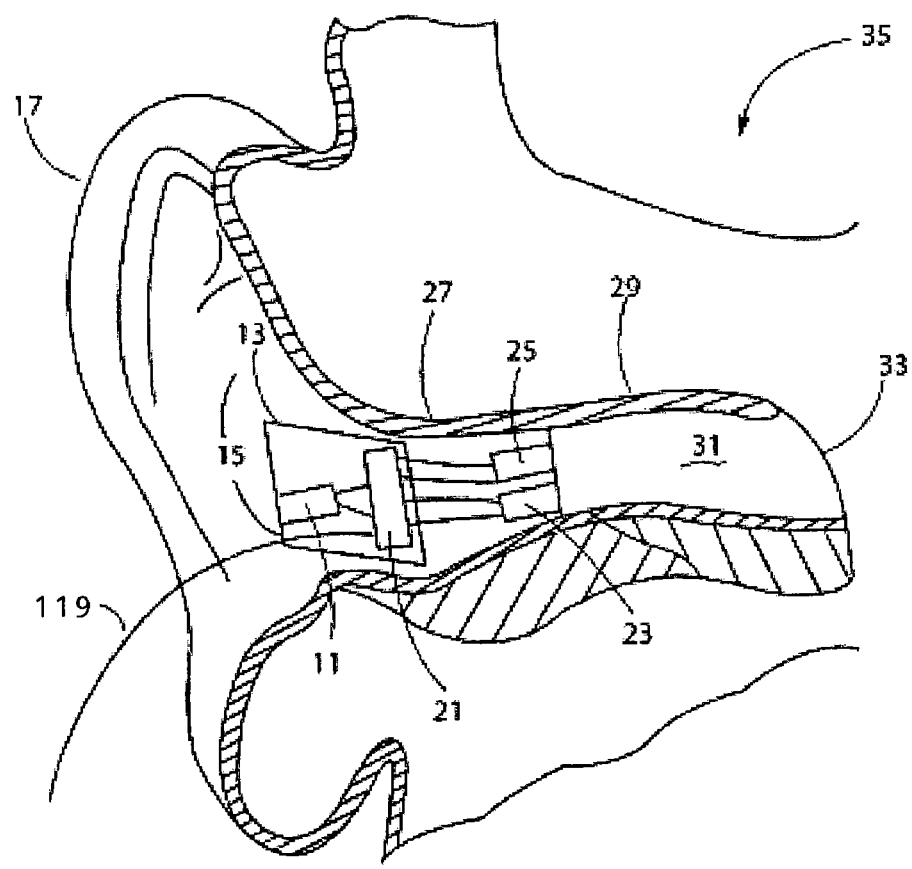
FIG. 2 is a block diagram of the system in accordance with at least one exemplary embodiment of the invention in situ in the ear.

At least one exemplary embodiment of the invention is directed to measuring and determining the exposure of sound to the ear over time. Reference is made to FIG. 1 in which a system, generally indicated as 100, is constructed in accordance with at least one exemplary embodiment of the invention. System 100 includes an audio input device 113 for receiving sound at the ear. As will be discussed below, audio input device 113 can include an analog audio input 11, 23 and a digital audio input 19. In at least one exemplary embodiment, audio input device 113 receives audio input from at least one of three sources, namely; ambient noise around the ear, direct input noise such as a MP3 player or other device which can produce a digital audio input at digital audio input 19, and noise as detected within the ear canal 31 (FIG. 2). The audio input device 113 outputs an audio signal corresponding to the received sound. Analog output signals from analog audio inputs 11, 23 are converted to a digital signal by an analog-to-digital (A/D) converter 118 so that digital sound signals are input into an input level detector 120.

Input level detector 120 determines the sound pressure level of the sound received at audio input device 113. Input level detector 120 outputs a sound pressure level (SPL) signal, which is input to a minimum-level threshold detector 122. Minimum level threshold detector 122 determines whether or not the sound pressure level as detected by input level detector 120 exceeds a minimum level threshold. As will be discussed below, the minimum level threshold can be the PSL (e.g., effective quiet level) of the individual, or some predetermined level substantially corresponding to a level which is ear damage neutral over time or a level of interest, such as 80 dB, because of its effect on the ear. Therefore, if the minimum level threshold is detected as being exceeded, a signal indicating a sound pressure level in excess of the minimum level threshold is output to a start timer 124, which triggers a digital timer system 126 to begin a clock. Conversely, if the input sound pressure level is detected as being below the minimum threshold, a signal indicating the sound pressure level is below the minimum level threshold is output to a start timer 124, which triggers a digital timer system 126 to begin a clock of a restorative period. If the sound pressure level is at the minimum threshold (within a margin of error), no clock needs to be started because this is neutral to the desired effect. In a preferred embodiment, the clock signal is changed with every significant (more than 1 dB by way of example) change in sound pressure level to get an accurate profile of sound exposure over time.

Once the sound pressure level as detected at input level detector 120 decreases to or is below the minimum threshold level, a stop timer signal is output from stop timer 128 to digital timer system 126 to stop the clock corresponding to exposure to the excessively intense level. Digital timer system 126 outputs a clock value corresponding to the time period at which the minimum level threshold was not met, or in the preferred embodiment, for each period corresponding to a discrete level change.

A data memory or learning history database 127 receives the clock value from digital timer system 126 as well as the actual input level detected at input level detector 120 and determines a listening history or sound pressure level exposure history. The sound pressure level exposure history is a record of the user's exposure to sound pressure levels over time. Because the effect of exposure is cumulative, it is important that the exposure history be maintained. The listening history, as will be discussed below, can include real ear level data, listening duration data, time between listening sessions, absolute time, sound pressure level dose (SPL Dose) data, including any restorative sound level, number of acoustic transients and crest factor and other data.

The sound pressure level exposure history or listening history includes both the listening habits history and the environmental or ambient noise exposure history. The environmental noise exposure history is the exposure of a user to environmental noise over time as a result of the auditory stimuli inherent to the environment where the user is present. This can be highway traffic, construction site, even the restorative effect of the quiet sound pressure levels, e.g., those typically encountered in a library whereas, the listening habits history is associated for the purposes for this disclosure with user-directed auditory stimuli such as music, words, other noises, which a user intentionally encounters for a purpose such as communication, learning, and enjoyment. Therefore, database 127, as will be discussed below, stores the cumulative SPL exposure.

It should be noted that in at least one exemplary embodiment, minimum level threshold detector 122 also starts the timer 124 when the sound pressure level is below the predetermined level. In this way, the restorative effect of below PSL (e.g., effective quiet noise) is accumulated for determining overall exposure damage potential.

In effect, the only time that digital timer system 126 is not running is when the detected sound pressure level signal is at the minimum level threshold. A listening fatigue calculator 130 receives the input level signal from input level detector 120 and data from the data memory listening history 127, and determines whether or not listening fatigue or hearing damage is likely to occur as a result of further exposure. Hearing damage is the injury to the hearing mechanism including conductive and sensorineural decrement in hearing threshold levels. It can be either temporary or permanent so long as it is a result of the noise exposure is above PSL (e.g., Effective Quiet). In other words, listening fatigue calculator 130 will output a signal when a threshold sound exposure, determined as a function of exposure time and sound pressure level, as will be discussed in greater detail below, is achieved. At that point, a listening fatigue signal is output.

It should be noted that in an alternative embodiment, system 100 can make use of an ambient noise detection/cancellation system 142 as known in the art. These systems produce signals, which cancel sound pressure levels at certain frequencies and/or certain levels to reduce the effect of undesired noise, whether environmental noise or user directed noise. It will have some effect in elongating the permissible exposure time by negating the sound pressure level detected by input level detector 120.

In at least one exemplary embodiment, the signal from the listening fatigue calculator is utilized to prevent damage and encourages some action by the user when exposure levels are near damaging levels. Therefore, in one non-limiting example, a listening fatigue display 140 is provided for receiving the signal from the listening fatigue calculator and displaying to the user a prompt to discontinue exposure to the sound level from the damaging sound source or audio source.

In another non-limiting example, the signal from the listening fatigue calculator is output to an audio warning source 132, which outputs an output audio warning to the user notifying the user that exposure to the sound source has reached critical levels.

In at least one exemplary, but non-limiting, embodiment, as will be discussed below, system 100 includes an output acoustical transducer 25 to provide an audio signal to the ear. Output acoustical transducer 25 operates under the control of a digital signal processor (DSP) 134. Digital signal processor 134 receives a digital audio signal from input level detector 120, which acts as a pass through for the digitized signals from audio input device 113. Digital signal processor 134 passes the sound signals through to a digital to analog (D/A) converter 136 to drive acoustical transducers 25 to recreate the sound received at audio input device 113 inside the ear canal 31 in at least one exemplary embodiment of the invention as shown in FIG. 2. With such an exemplary embodiment, audio warning source 132 provides an output to digital sound processor 134 causing output acoustical transducer 25 to output a warning sound inside the ear of the user.

Additionally, in at least one further exemplary embodiment, listening fatigue calculator 130 outputs a listening fatigue signal to digital processor 134 which causes digital signal processor 134 to attenuate the sound signal prior to output to acoustical transducer 25 to reduce the signal output level by any of the linear gain reduction, dynamic range reduction, a combination of both, or a complete shutdown of transducer 25. Attenuation would be at least to the level, if not below, the PSL (e.g., effective quiet level) to allow for ear recovery prior to damage.

It should be noted, that because personal hearing threshold and discomfort levels can change from person to person, and because both of the time intervals are a function of many variables, in a non-limiting example, to provide a dynamic ever-changing response, system 100 operates under software control. The configuration of the digital sound processor 134, listening fatigue calculator 130, the minimum level threshold detector 122, and the input level detector 120 are operated under software control.

In an exemplary embodiment of the invention, the control programs are stored in a program memory 148 for operating the firmware/hardware identified above. Furthermore, the program stored within memory 148 can be personalized as a result of testing of the user's ear, or by other modeling methods, in which system 100 includes a software interface 144 for receiving online or remote source updates and configurations. The software interface 144 communicates with a data port interface 146 within system 100, which allows the input of software updates to program memory 148. The updates can be transmitted across a distributed communications network, such as the Internet, where the updates take the form of online updates and configurations 143.

It should be noted that there is multiple functionality distributed across system 100. In at least one exemplary embodiment, at least audio input device 113 and acoustical transducer 25 are formed as an earpiece, which extends into the outer ear canal so that the processing of signals pertains to sound received at the ear. However, it is well within the scope of at least one exemplary embodiment of the invention to provide substantially all of the functionality in an earpiece so that system 100 is a "smart device."

Also note that when referring to measurements in decibels (dB), one is referring to a logarithmic ratio. For example dB is defined as:

$$SPL = \beta(dB) = 10\log\frac{I}{I_0} = 10\log\frac{\Delta P^2}{\Delta P_0^2} \qquad (1)$$

Where I is the intensity measured, $I_0$ is a reference intensity, $I_0 = 10^{-12}$ W/m$^2$, and $P_0$ is a reference pressure, $\Delta P_0 = 20$ micropascals, and where $\Delta P$ is the root mean squared pressure amplitude in a measured pressure wave (e.g., using a transducer). Thus, the sound pressure level (SPL) can be measured in dB.

Alternatively one can use the above equation and solve for measured pressures instead. For example:

$$\Delta P(t) = 10^{(sPL(t)/20.0)}\Delta p_0 \qquad (2)$$

In the discussion of formulas herein we refer to SPL as a non-limiting example and one of ordinary skill in the arts could re-derive the equations in terms of measured pressures, $\Delta P$, both are intended to lie within the scope of at least one exemplary embodiment. Reference is now made to FIG. 2 in which system 100 in which the transducer configuration, that portion of system 100, which converts sound pressure level variations into electrical voltages or vice versa is shown. In this embodiment, acoustic transducers include microphones as an input and loudspeakers as an acoustical output.

FIG. 2 depicts the electro acoustical assembly 13 (also referred to herein as an in-the-ear acoustic assembly 13 or earpiece 13), as it would typically be placed in the ear canal 31 of ear 17 of user 35. The assembly is designed to be inserted into the user's ear canal 31, and to form an acoustic seal with the walls 29 of the ear canal 31 at a location 27, between the entrance 15 to the ear canal 31 and the tympanic membrane or eardrum 33. Such a seal is typically achieved by means of a soft and compliant housing of assembly 13. A seal is critical to the performance of the system in that it creates a closed cavity in ear canal 31 of approximately 0.5 cc in a non-limiting example between the in-ear assembly 13 and the ear's tympanic membrane 33.

As a result of this seal, the output transducer (speaker) 25 is able to generate a full range bass response when reproducing sounds for the system user. This seal also serves to significantly reduce the sound pressure level at the user's eardrum 33 resulting from the sound field at the entrance 15 to the ear canal 31. This seal is also the basis for the sound isolating performance of the electroacoustic assembly 13. Located adjacent to speaker 25, is an ear canal microphone (ECM) 23, which is also acoustically coupled to closed cavity 31. One of its functions is that of measuring the sound pressure level in cavity 31 as a part of testing the hearing sensitivity of the user as well as confirming the integrity of the acoustic seal and the working condition of itself and speaker 25. Audio input 11 (also referred to herein as ambient sound microphone (ASM) 11) is housed in assembly 13 and monitors sound pressure at the entrance 15 to the occluded ear canal. The transducers can receive or transmit audio signals to an ASIC 21 that undertakes at least a portion of the audio signal processing described above and provides a transceiver for audio via the wired or wireless communication path 119.

In the above description the operation of system 100 is driven by sound pressure level, i.e. sound levels are monitored for time periods or epochs during which the sound pressure level does not equal the minimum level threshold or is constant. However, as will be discussed in connection with the next exemplary embodiments of the invention, system 100 can also operate utilizing fixed or variable sampling epochs determined as a function of one or more of time and changes in sound pressure level, sound pressure dosage level, weighting functions to the sound pressure level, and restorative properties of the ear.

Figure 3:
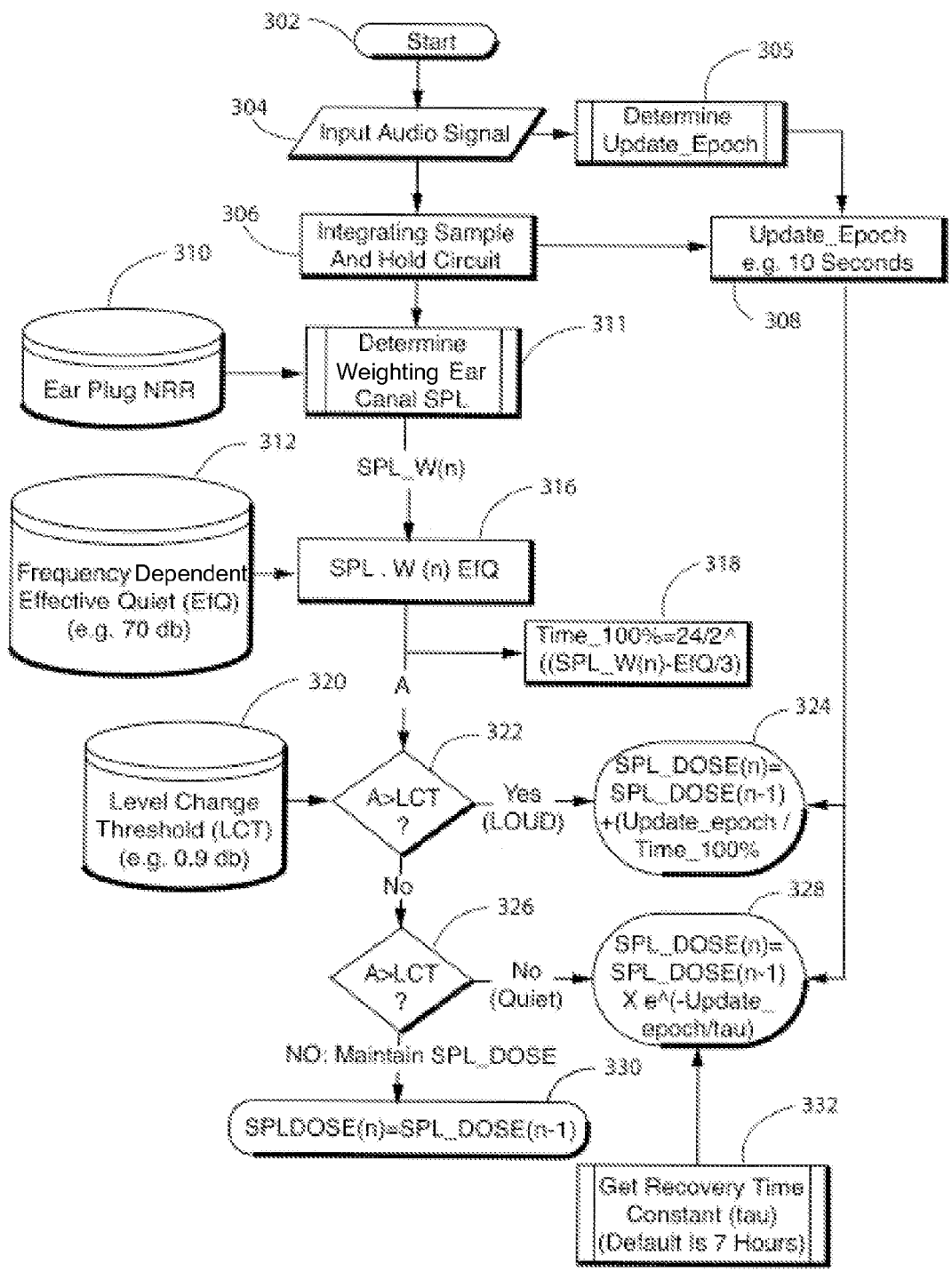
FIG. 3 is a flow chart for calculating listening fatigue in accordance with at least one embodiment of the invention by measuring a quantity (e.g., the sound pressure level) over time as perceived at the ear.

Reference is now made to FIG. 3 in which a flow chart for monitoring the sound pressure level dose at various sample times n is provided. The process is started in a step 302. An input audio signal is generated in a step 304 at either the ear canal microphone (ECM) 23 or the ambient sound microphone (ASM) 11. Changes in SPL_Dose resulting from duration of exposure time is a function of the sound pressure level, therefore, the epoch or time period used to measure ear exposure or, more importantly, the time-period for sampling sound pressure level is determined in a step 305. The update epoch is used in the SPL Dose function determination as well as to effect the integration period for the sound pressure level calculation that, as will be discussed below, is used to calculate the weighted ear canal sound pressure level.

Figure 6:
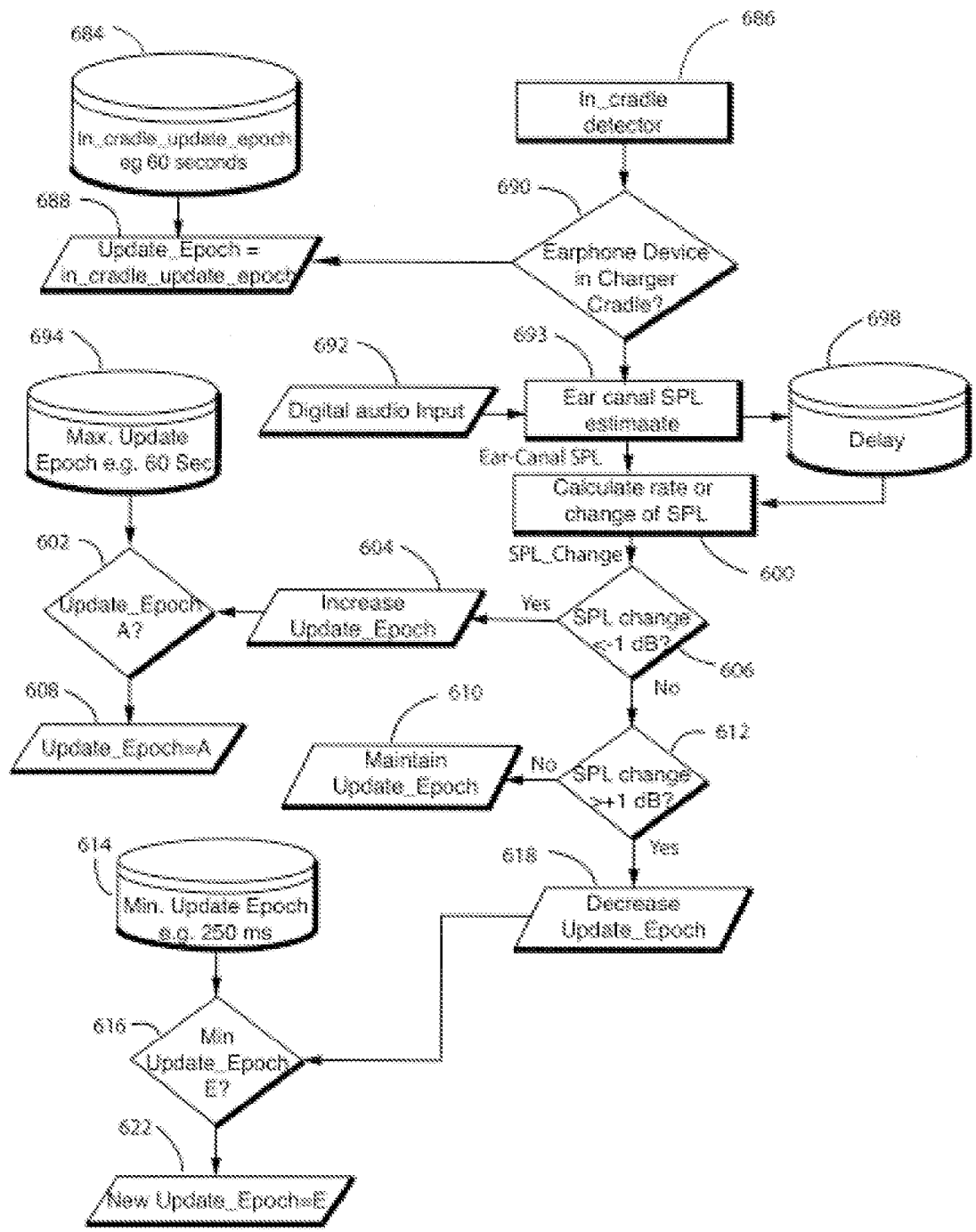
FIG. 6 is a flow chart for determining an update epoch in accordance with at least one exemplary embodiment of the invention.
Figure 7:
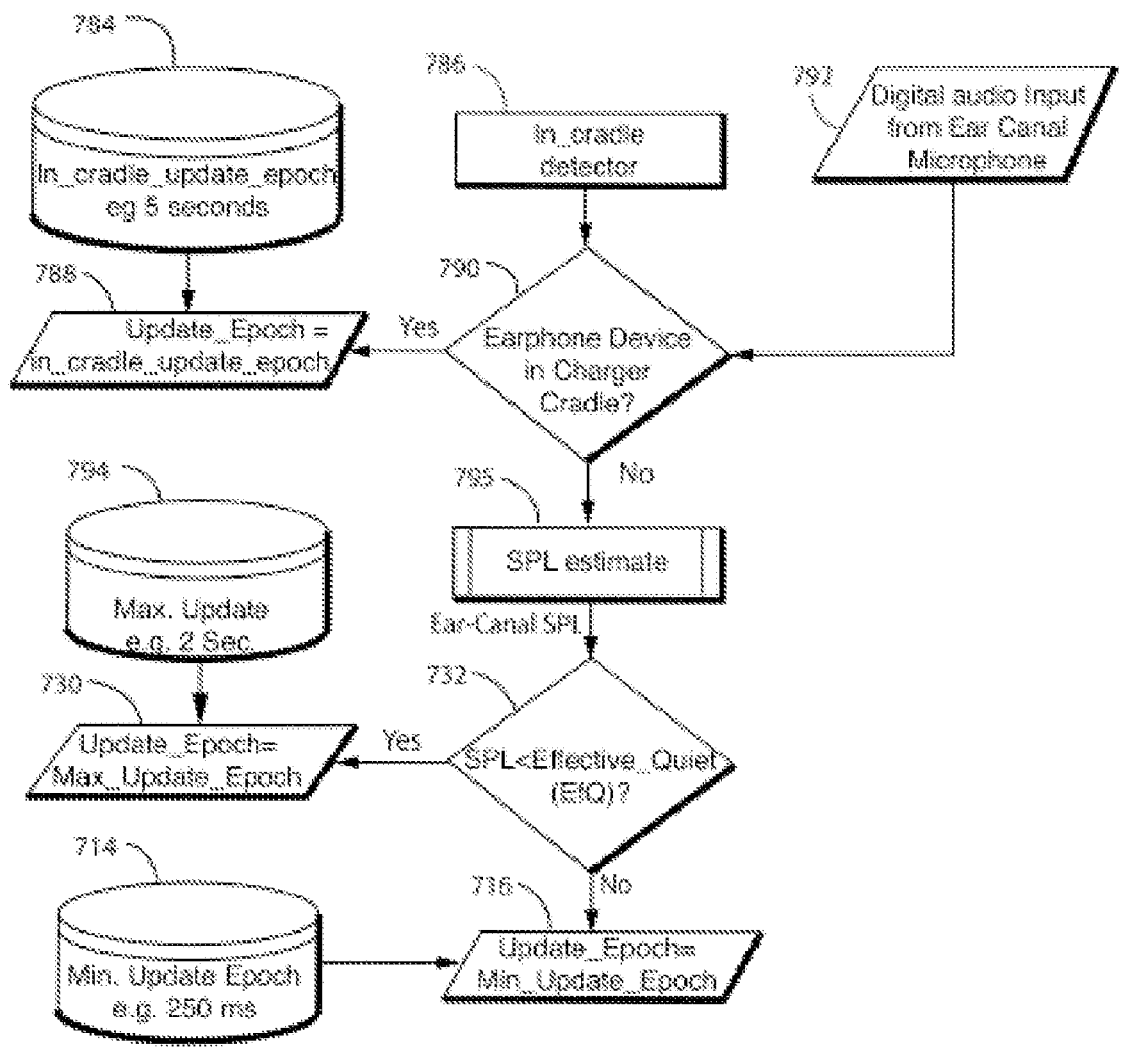
FIG. 7 is a flow chart for determining an update epoch in accordance with yet another exemplary embodiment of the invention.

Reference is now made to FIGS. 6 and 7. In FIG. 6, a method is defined to change the update epoch as a function of the weighted ear canal sound pressure level, which will be discussed in greater detail below. System 100 is capable of determining when earpiece 13 is in a charger or communication cradle (i.e., not in use in the ear of the user). In a step 684, a predetermined standard is provided for the update epoch, 60 seconds in this example. In step 688, the update epoch is set as the in-cradle update epoch. The in-cradle state is detected in step 686. If it is determined in a step 690 that earpiece 13 (also referred to herein as earphone device 13) is in a charger or cradle mode, then the update epoch is set as the in-cradle epoch; in the step 688.

However, if in step 690 it is determined that the earphone device 13 is in use, in other words "not in the cradle", then, by default, an audio signal is input to earpiece 13 in step 692. In step 693, an ear canal sound pressure level is estimated as a function of the audio input at step 692. The current (n) ear canal sound pressure level estimate is stored as a delay level in a step 698. An audio input is determined at a later time when step 692 is repeated so that a second in-time ear canal sound pressure level estimate is determined.

In a step 600, the delayed (n−1) or previous sound pressure level is compared with the current (n) ear canal sound pressure level estimate to calculate a rate of change of the sound pressure level. The change level is calculated in units of dB per second. This process of step 692 through 600 is periodically repeated.

In a step 606, it is determined whether or not the sound pressure level change is less than a predetermined amount (substantially 1 dB by way of non-limiting example) between iterations, i.e., since the last time the ear canal sound pressure level is calculated. If the change is less than the predetermined amount, then in step 604 the update epoch is increased. It is then determined in a step 602 whether or not the epoch update is greater than a predefined amount D set in step 694 as a maximum update epoch such as 60 seconds in a non-limiting example. If in fact, the update epoch has a value greater than the maximum update epoch D then the update epoch is set at the higher value D in step 608.

If it is determined in step 606 that the sound pressure level change is, in a non-limiting example, greater than −1 dB, but less than +1 dB as determined in step 612, then the update epoch value is maintained in a step 610. However, if it is determined that the sound pressure level change is, in a non-limiting example, greater than +1 dB, then the update epoch value is decreased in a step 618 to obtain more frequent sampling. A minimum predetermined update epoch value such as 250 microseconds is set in a step 614. If the decreased update epoch determined in step 618 is less than, in other words an even smaller minimum time-period than the predetermined minimum update epoch E, then the new update epoch is set as the new minimum update epoch value in steps 616 and 622. In this way, the sample period is continuously being adjusted as a function of the change in sound pressure level at the ear. As a result, if the noise is of a transient variety as opposed to a constant value, the sampling interval will be changed to detect such transients (e.g., spikes) and can protect the ear.

Reference is now made to FIG. 7 in which a method for changing the update epoch is illustrated as a function of the way that the ear canal sound pressure level estimate is provided. Again, in accordance with at least one exemplary embodiment of the invention, the update epoch is decreased when the ear canal sound pressure level is high or increasing.

The difference between the embodiment of FIG. 7 and the embodiment of FIG. 6 is that the update epoch is not continuously adjusted, but is more static. If the ear canal sound pressure level is less than PSL (e.g., effective quiet, a decibel level which when the ear is exposed to over time does not damage or restore the ear), then the update epoch is fixed at a predefined maximum epoch value and this is the value used by system 100 as will be discussed in connection with FIG. 3 below. In this embodiment, if the ear canal sound pressure level is determined to be greater than a permissible (or permitted) sound level (PSL) (e.g., effective quiet), then the update epoch is fixed at a shorter minimum value and this is returned as the update epoch to be utilized.

In FIG. 7, specifically, as with FIG. 6, an in-cradle update epoch of 5 seconds by way of non-limiting example, is stored in system 100 in a step 784. In a step 788, the initial update epoch is set as the in-cradle update epoch. A maximum update epoch time, such as 2 seconds by way of non-limiting example, is stored in a step 794. In a step 714, an initial minimum update epoch (250 microseconds in this non-limiting example) is stored.

In a step 786 and step 790 it is determined whether or not system 100 is in a non-use state, i.e., being charged or in a cradle. If so, then the update epoch is set at the in-cradle update epoch. If not, then a digital audio signal is input from ear canal microphone 23 in step 792. A sound pressure level is estimated in step 795. It is then determined whether or not the ear canal sound pressure level is less than PSL (e.g., effective quiet) in a step 732. If the sound pressure level is less than the PSL (e.g., effective quiet) as determined in step 732, then the update epoch is set at the maximum update epoch in a step 730. If the sound pressure level is louder than the effective quiet, then in step 716, the update epoch is set to the minimum update epoch.

Returning to FIG. 3, in a non-limiting exemplary embodiment, the update epoch is set at 10 seconds in a step 302 utilizing either a constant predetermined sample time, or either of the methodologies discussed above in connection with FIGS. 6 and 7. In a step 306, the input audio signal is sampled, held, and integrated over the duration of the epoch as determined in step 308. As a result, the update epoch affects the integration period utilized to calculate the sound pressure level dose as a function of the sound pressure level and/or as the weighted ear canal sound pressure level.

In a step 310, an earplug noise reduction rating (NRR) is stored. The noise reduction rating corresponds to the attenuation effect of earpiece 13, or system 100, on sound as it is received at audio input 11 and output at the output transducer 25 or as it passes from the outer ear to the inner ear, if any exemplary embodiment has no ambient sound microphone 11. In a step 311, a weighted ear canal sound pressure level is determined, partially as a function of the earplug noise reduction rating value.

Figure 4:
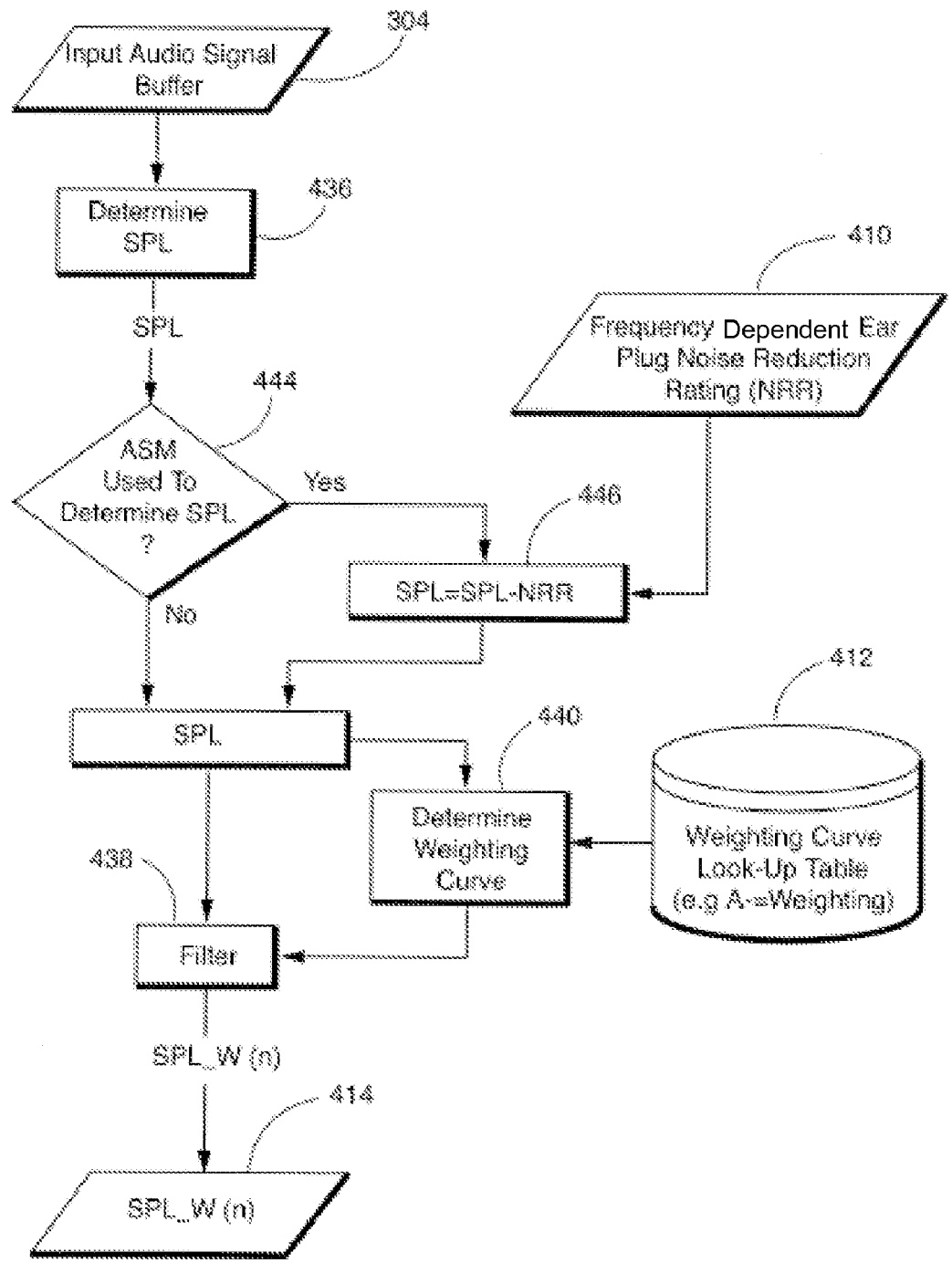
FIG. 4 is a flow chart for determining a weighted ear canal sound pressure level in accordance with another exemplary embodiment of the invention.

Reference is now made to FIG. 4 where a method for determining the weighted ear canal sound pressure level in accordance with at least one exemplary embodiment of the invention is illustrated. Like numerals are utilized to indicate like structure for ease of discussion and understanding. Weighting is done to compensate for the manner in which sound is perceived by the ear as a function of frequency and pressure level. As sounds increase in intensity, the ear perceived loudness of lower frequencies increases in a nonlinear fashion. By weighting, if the level of the sound of the field is low, the methodology and system utilized by at least one exemplary embodiment of the invention reduces the low frequency and high frequency sounds to better replicate the sound as perceived by the ear.

Specifically, a weighting curve lookup table, such as A-weighting, acts as a virtual band-pass filter for frequencies at sound pressure levels. In a step 304, the audio signal is input. In step 410, frequency-dependent earplug noise reduction ratings are stored. These values are frequency-dependent and in most cases, set as manufacturer-specific characteristics.

As discussed above, in a step 306, the input audio signal is shaped, buffered and integrated over the duration of each epoch. The sound pressure level of the shaped signal is then determined in a step 436. It is determined whether or not ambient sound microphone (ASM) 11 was utilized to determine the sound pressure level in a step 444. If microphone 11 was utilized, then the frequency-dependent earplug noise reduction rating of earpiece 13 must be accounted for to determine the sound level within the ear. Therefore, the noise reduction rating, as stored in step 310, is utilized with the sound pressure level to determine a true sound pressure level (at step 446) as follows:

$$SPL_{ACT} = SPL - NRR; \quad (3)$$

where sound pressure $SPL_{ACT}$ is the actual sound pressure level received at the ear medial to the ECR, SPL is the sound pressure level determined in step 436 and NRR is the noise reduction rating value stored in step 410.

If the ambient sound microphone (ASM) 11 is not used to determine the sound pressure level then the sound pressure level determined in step 436 is the actual sound pressure level. So that:

$$SPL_{ACT} = SPL \quad (4)$$

It is well within the scope of at least one exemplary embodiment of the invention to utilize the actual sound pressure level as determined so far to determine the affect of the sound pressure level received at the ear on the health of the ear. However, in at least one exemplary embodiment, the sound pressure level is weighted to better emulate the sound as received at the ear. Therefore, in a step 412, a weighting curve lookup table is stored within system 100. In a step 440, the weighting curve is determined as a function of the actual sound pressure level as calculated or determined above in steps 436, 446 utilizing a weighting curve lookup table such as the A-weighting curve. The A-weighting curve is then applied as a filter in step 438 to the actual sound pressure level. A weighted sound pressure level value representative of a sampled time period (SPL_W(n)) is obtained to be utilized in a step 414.

The weighting curve can be determined in step 440 by applying a frequency domain multiplication of the sound pressure level vector and the weighting curve stored in step 412. In this exemplary embodiment the weighting curve would be appropriate for direct multiplication with the SPL in the frequency domain (i.e., SPL(f)). In another exemplary embodiment the weighted SPL can be expressed as a weighting of the measured pressure vector as:

$$SPL\_W(n)(t) = 20 \log\left(\frac{\Delta P^{W_A}(t)}{\Delta P_0}\right) \quad (5)$$

where $\Delta P(t)$ is the measured temporal change in root mean squared pressure, which can be converted into spectral space (e.g., FFT) as $\Delta P(f)$ which is the measured spectral change in pressure, which can in turn be multiplied by a weighting function (e.g., A-weighting), $W_A(f)$) and expressed as $\Delta P^{W_A}(f) = \Delta P(f) \cdot W_A(f)-$, and then reconverted (e.g., inverse FFT) into temporal space to obtain $\Delta P^{W_A}(t)$. To obtain a single value various integration or summation over the n-th time interval (e.g., which can change in time) can be performed. For example:

$$SPL\_W(n) = \frac{1}{\Delta t_n} \int_{t_{n-1}}^{t_n} 10 \log\left(\frac{(\Delta P^{W_A}(t))^2}{\Delta P_0^2}\right) dt \quad (6)$$

The time during which a user may be exposed to the sound level SPL_W(n), i.e. the time to 100% allowable dosage at SPL level SPL_W(n), is referred to below as Time__100% (n).

The weighting curves can be stored as a lookup table on computer memory, or can be calculated algorithmically. Alternatively, the input audio signal can be filtered with a time or frequency domain filter utilizing the weighting curve stored in step 412 and the sound pressure level as calculated. For low-level sound pressure levels, those less than 50 dB, by way of non-limiting example, a weighting curve, which attenuates low and high frequencies can be applied (similar to an A-weighting curve). For higher sound pressure levels, such as more than 80 dB, by way of non-limiting example, the weighting curve can be substantially flat or a C-weighting curve. The resulting weighted ear canal sound pressure level during any respective sampling epoch is returned as the system output SPL_W(n) in step 414. Note that herein various conventional weighting schemes are discussed (e.g., A-weighting, C-weighting) however in at least one exemplary embodiment non-conventional weighting schemes can be used. For example, generally the threshold level of hearing sensitivity (threshold of detection) is referenced in dB, where 20 micropascals is typically used as the minimum threshold level of pressure variation that an average person can detect. This reference value tends to be used at all frequencies, although the threshold level varies with frequency. Thus, one weighting scheme is to adjust the reference 0 dB level on a frequency basis, by using a conventional dB of threshold hearing chart, which provides the dB (f) at threshold level. A weighting function can be used where the value is about 1 at the reference value (e.g., equivalent to 20 micropascals) at a reference frequency (e.g., 1000 Hz). The other values (e.g., as a function of frequency) of the weighting function can vary depending upon the reference threshold pressure variation for the particular frequency, for example if at 30 Hz the threshold level in dB is 65 dB, then the weighting value can be $\frac{1}{65}$ at 30 Hz, de-emphasizing the loudness and/or intensity at 65 dB when SPL Dose (f) is calculated.

Returning to FIG. 3, a safe listening time is calculated by comparing the weighted sound pressure level with the PSL (e.g., effective quiet level) in step 316. Therefore, a value A corresponding to how far from safe listening the sound pressure level is, is determined by the equation:

$$A = SPL\_W(n) - PSL \quad (7)$$

where PSL is the permissible sound level, for example PSL=EfQ, where EfQ is equal to the sound level of effective quiet (as stored at step 312). However PSL can be any level chosen for the particular circumstance, for example lower than EfQ.

By utilizing this simple comparative function, fewer machinations and processes are needed. System 100 takes advantage of the fact that because the PSL (e.g., effective quiet level) can be neutral to the ear, sound pressure levels significantly above the PSL (e.g., effective quiet level) are generally damaging and noise levels below the PSL (e.g., effective quiet) generally allow for restoration/recovery.

In a step 318, the remaining safe listening time at the beginning of any current sampling epoch can be calculated by Time__100% minus the time duration of exposure up to the current sampling epoch. Note that a negative number can occur, indicating that no safe listening time remains. The estimated time (e.g., in hours) until the individual's sound exposure is such that permanent threshold shift may occur, ignoring any previous sound exposure and assuming that the SPL of the sound field exposed to the individual remains at a constant level L can be calculated as follows:

$$\text{Time\_100\%}(n) = T_c/(2^{((SPL\_W(n)-PSL)/ER)}); \quad (8)$$

Where PSL is the permissible sound level, and Tc is the critical time period. For example, if Tc (Critical Time) is 8 hours and PSL is 90 dBA, then that accepts that ~22-29% of people are at risk for hearing loss. If Tc is 8 hours and PSL is 85 dBA, then that accepts that ~7-15% of people are at risk, likewise for if Tc is 24 hours and PSL is 80 dBA, same 7-15% at risk. Thus Time__100% (n) reflects a reduction of the risk to a chosen level. Note that $T_c$ is the critical time period of exposure that one is looking at (e.g., 8 hours, 24 hours), and ER is the exchange rate, for example can be expressed as:

$$\text{Time\_100\%}(n) = 8(\text{hours})/(2^{((SPL\_W(n)-85\text{ dBA})/3\text{ dB})}) \quad (9)$$

These values assume a recovery period of 16 hours at a SPL level during that time of less than 75 dBA (where dBA refers to Decibels of an A-weighted value). Of course the realism of such an assumption is questionable given music, TV, and other listening habits of individuals. Thus, we are concerned with exposure over a 24 hour period. Thus, Time__100% (n) can be expressed for a 24 hour period (e.g., $T_c$=24 (hours)), where, for example using an equal energy assumption (i.e., ER of 3 dBA), as:

$$\text{Time\_100\%}(n) = 24/(2^{((SPL\_W(n)-PSL)/3)}). \quad (10)$$

Another further example is the situation where PSL=EfQ, where the Effective Quiet, EfQ is defined as the highest sound level that does not cause temporary or permanent hearing threshold shift, nor does it impede recovery from temporary hearing threshold shift. For broadband noise, it can be 76-78 dBA, although these numbers can be different or refined over time based upon research and/or measurement history.

As a non-limiting example, the lower bound of SPL_W(n) dictating the Time__100% equation would be SPL_W(n)=PSL, and the upper bound of the SPL_W(n) dictating Time__100% equation would be about SPL_W(n)=115 dB.

Note that in at least one exemplary embodiment, the acoustic signals measured by an ECM or an ECR in ECM mode, can be used to detect a user's voice, for example using the technology discussed in Webster et al., U.S. Pat. No. 5,430,826, incorporated by reference in its entirety. If voice is detected then by the magnitude of the SPL (e.g., 80 dB) one can tell whether the user is speaking as compared to a non-user's voice (e.g., 50 dB) that has been attenuated by the earpiece. When a user's voice is detected then SPL_W(n) can be reduced by an amount (DSPL, e.g., 20 dB) that is due to Stapedius Reflex (e.g., when the user's voice triggers a muscle response in the muscles supporting the bones transmitting sound from the eardrum to cochlea), effectively damping some of the sound. Thus $SPL\_W(n)_{new}$=SPL_W(n)-DSPL, where $SPL\_W(n)_{new}$ is used in the Time__100% (n) equation as opposed to SPL_W(n).

In this embodiment, rather than make use of the Sound Level (L), the period is a function of the loudness and quietness of the weighted sound pressure level. It should be noted that PSL (e.g., effective quiet) is used in the above example, but any level of interest, such as 80 dB, or no sound level, i.e., SPL_W(n)-0, can be used. The weighted sound pressure level and PSL can be expressed as a frequency-dependent numerical array or a value scalar.

It is next determined whether or not the difference between the current weighted sound pressure level and the PSL (e.g., effective quiet) is above a tolerable threshold for risk of hearing damage or not, i.e., whether the weighted SPL in the eardrum is considered to increase risk for hearing damage or not. A sound pressure level dose is calculated depending upon whether the sound level is loud or not. The sound pressure level dose (SPL Dose) is the measurement, which indicates an individual's cumulative exposure to sound pressure levels over time. It accounts for exposure to direct inputs such as MP3 players, phones, radios and other acoustic electronic devices, as well as exposure to environmental or background noise, also referred to as ambient noise. The SPL Dose is expressed as a percentage of some maximum time-weighted average for sound pressure level exposure.

Because the sound pressure level dose is cumulative, there is no fixed time-period for ear fatigue or damage. At or below effective quiet, the sound pressure level exposure time would theoretically be infinite, while the time period for achieving the maximum allowable sound pressure level dose becomes smaller and smaller with exposure to increasingly more intense sound. A tolerable level change threshold corresponding to the amount of noise above or below the effective quiet which has no great effect on the ear as compared to effective quiet is determined and stored in memory 127 in a step 320. In a step 322, the differential between the weighted sound pressure level and the effective quiet is compared to the level change threshold.

A differential value A, corresponding to the level change, can be calculated as follows:

$$A = SPL\_W(n) - PSL \quad (11)$$

If A is greater than the level change threshold, the noise is considered to increase risk for hearing damage and the sound pressure level dose is calculated in a step 324 as follows:

$$SPL\ Dose(n) = SPL\ Dose(n-1) + (Update\_Epoch(n)/Time\_100\%) \quad (12)$$

where SPL Dose(n−1) is the SPL Dose calculated during the last epoch; Update_Epoch is the time (in hours) since the last SPL Dose was calculated. As described above, Update_Epoch can be adaptive, e.g., shortened when the sound pressure level is louder; and Time_100% (n), the time period remaining for safe exposure is determined by the equation:

$$Time\_100\%(n) = 24\ hours/(2^{((L-PSL)/3)}) \quad (13)$$

where L=sound level (in dB) of the combination of environmental noise and audio playback. It should be noted that sound level (L) can be substituted for SPL_W(n).

It should be noted, as can be seen from the equation, that the time value becomes more important than the sound pressure level as updates are spread apart. However, this is to protect overexposure to harmful sounds because a less accurate sample size must account for the unknown. The wider the periodicity, the less accurate determination of actual exposure. Infrequent updates of the SPL Dose assume a relatively constant sound level, ignoring transients (e.g. spikes) and intervening restorative periods. Accordingly, sound pressure level and epoch periodicity are weighed against each other to protect the ear.

If in step 322 it is determined that the differential is not greater than the level change threshold, including negative values for A (which are restorative values), then in step 326 it is determined whether or not the differential, as determined in step 316, is less than the level change threshold in a step 322. If it is determined that the differential is not less than the level change threshold, then the received noise was the effective quiet level, i.e., the level change threshold equals zero and in a step 330, the current SPL Dose is maintained at the same level. There is no change to the dose level. However, if the differential A is less than the level change threshold then this is a restorative quiet as determined in step 326. Thus, if the differential A (e.g., A=SPL_W(n)−PSL) is less than zero, within measurement error, then this is considered a restorative quiet, then the n-th SPL dose is determined as (at step 328)

$$SPL\ Dose(n) = SPL\ Dose(n-1) * e^{(-Update\_epoch/\tau)} \quad (14)$$

Where: $\tau$ (referred to as "tau" in the following diagrams) can vary (e.g., equal to about 7 hours). In some exemplary embodiments, tau is adaptive for different users. In at least one exemplary embodiment, the level change threshold (e.g., measurement error) is set at substantially 0.9-1.0 dB.

Note that other forms of a recovery function can be used and the description herein is not intended to limit the recover function to an exponential relationship. For example, during lower exposure times (e.g., 102 minutes) some SPL values (e.g., 95 dB) can be used, if the subsequent SPL is less than PSL, in a linear manner (for example linearly decreasing until there is a near zero threshold shift at 4000 Hz after one day from the time at which SPL<PSL).

Another non-limiting example of a recovery function can be a combination over certain exposure and decay periods (e.g., 7 day exposure at 90 dB, with an initial threshold shift after the 7 days of about 50 dB at 4000 Hz). For example a slow decaying linear relationship can be applied for the first few hours (e.g., 2 hours) where SPL<PSL, then an exponential decay from after the first few hours to a few days (e.g., 4 days) after which a leveling trend can occur.

Additionally although a fractional increase in SPL Dose is given as a non-limiting example, SPL Dose increase can be linear or exponential depending upon the exposure SPL level and the duration. For example the growth can be linear at a certain SPL values (e.g., 95 dB) during different ranges of exposure time (e.g., for 95 dB, from about 4 minutes to 12 hours), then leveling out (e.g., threshold shift of about 59.5 dB) when the exposure time exceeds a certain length (e.g., for 95 dB about 12 hours).

In at least one exemplary embodiment the SPL values measured by an ECM (e.g., in an ECM mode) can be modified by a modification value (e.g., additive or multiplicative), for example $SPL_{new} = \beta SPL_{old} + \delta$, where the values, $\beta$ and $\delta$, can be time variant, positive or negative. Alternatively the values can be applied to the measured pressure values in a similar manner. One can convert the SPL measured by an ECM to free field values, which then can be compared to free field standards for damage risk criteria. For example Table 1 lists several frequency dependent responses of an earpiece while inserted, the "A" weighting curve offset, and the modification values $\beta$ and $\delta$.

TABLE 1

| Freq. (Hz) | Earpiece Freq. Resp. (dBSPL/V) | "A" weight offset (dB) | β (dB) | δ (dB) |
|---|---|---|---|---|
| 100 | 95 | −19.1 | 1.0 | 0.00 |
| 500 | 103.5 | −3.2 | 1.0 | −0.13 |
| 1000 | 104.0 | 0.0 | 1.0 | −1.83 |
| 2000 | 121.0 | 1.2 | 1.0 | −7.84 |
| 4000 | 106.0 | 1.0 | 1.0 | −15.57 |

Thus, for example an SPL (f) measured at 80 dB, at f=1000 Hz, would be subtracted by −1.83 to obtain a free field value to compare with damage-risk criteria, thus obtaining an $SPL_{new}$ of 78.13 dB. Note what is described is a non-limiting example, various other earpieces can have different values, and the SPL_DOSE equations, described herein, (e.g., SPL_Dose(n), Time_100%) can be based upon $SPL_{new}$. Note that further discussions concerning frequency responses and free field estimate (FFE) conversion can be viewed in U.S. Pat. No. 6,826,515, Bernardi et al. Alternatively ear canal dBA SPL (e.g., as measured by an ECM) may be converted to FFE dBA SPL using Table 1 of ISO 11904-1 (2002), incorporated herein by reference.

In step 332, the recovery time constant tau is determined. It may not be a function of exposure, but rather of recovery. It can be a default number or be determined as will be discussed below. As the SPL Dose is calculated by system 100, it is also monitored. Once the SPL Dose reaches a certain level, as it is a cumulative calculation, ear fatigue calculator 130 determines whether or not the SPL Dose corresponds to a fatigued ear, and if so, it outputs warnings as discussed in connection with FIG. 1.

Figure 5:
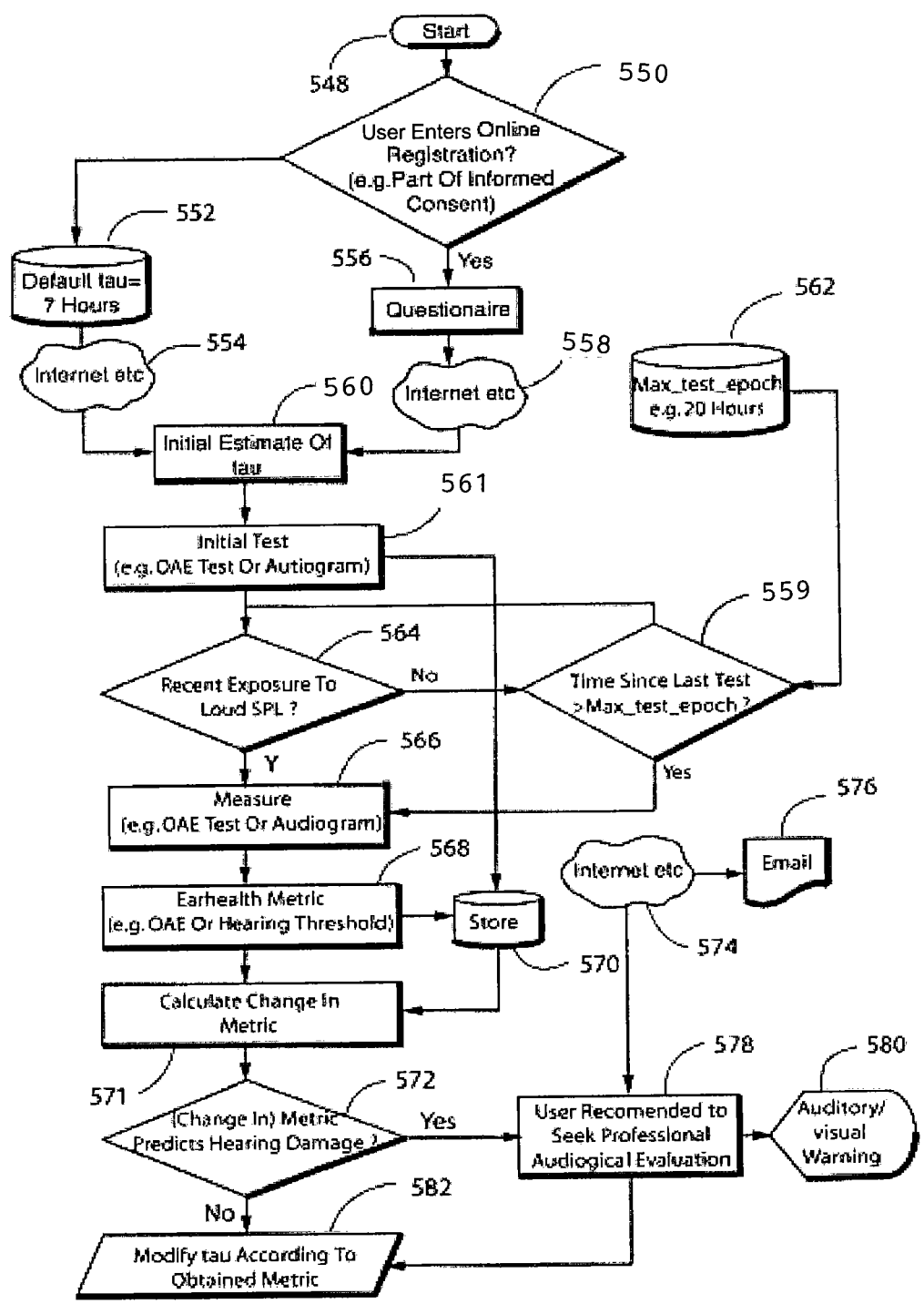
FIG. 5 is a flow chart for determining a personalized recovery time constant in accordance with another exemplary embodiment of the invention.

Reference is now made to FIG. 5 which depicts an optional methodology for not only updating the recovery time constant (tau) for individual users, but to provide additional methods for acting upon detected damaging exposure. The process is started at a step 548. In a step 550, it is determined whether or not the user wishes to make use of a registration process, for example online, for setting a personalized update epoch through communication with a remote registration system. If the user declines the registration, then the default tau is set at 7 hours in a step 552. In a step 554, this default value is transmitted to system 100 via a wired or wireless data communication network.

Alternatively, if the user registers in step 550, a questionnaire is presented in a step 556 in which the user informs system 100 regarding a user sound exposure history, age, work habits and other personal details that could affect the user's personal recovery function time, i.e., the time constant tau. The individual characteristics can be input to a formula or utilized as part of a look up table to determine the tau for the individual user. The estimate of tau determined in step 556 is transmitted to system 100 via a wireless or wired data communication system in a step 558. In step 560, the initial estimate of tau is set from the value determined in step 556 (or step 552).

An initial hearing test is performed in a step 561, which acquires data indicative of the user's hearing sensitivity. The test may be an otoacoustic emission (OAE) test or audiogram administered utilizing the ear canal receiver or speaker 25. However, the test can also be administered over the Internet, telephone or other communication device capable of outputting sounds sent across a distributed network and enabling responsive communication. The data is stored in a computer memory as an initial test value in a step 570 and is used in further processing to detect a change in the user hearing response.

In a step 564, it is determined whether the user has been recently exposed to intense sound pressure levels. This can be done utilizing the sound pressure level dose as stored or permanently calculated by system 100. If it is decided in step 564 that the user's ear canal sound pressure level is low, then in a step 559 it is determined whether the time since the last test is greater than a maximum test epoch. At the outset, the maximum test epoch is a set number determined in a step 562. In this non-limiting example, the maximum test epoch is set at 20 hours.

If it is determined that the time since the last test is greater than the maximum test epoch or, that there has been recent exposure to intense sound pressure level, then another test is administered in a step 566. The resulting test metrics are stored in steps 568, 570. In a step 571, the newly determined test metrics are compared to the initial test metrics to calculate any change in the metrics. In step 572, it is determined whether the change is predictive of hearing damage. If not, then in a step 582, the tau is modified according the obtained metric.

If it is determined that the hearing damage is predicted, then in a step 578 the user is recommended to remove themselves from the noise as discussed above with the operation of listening fatigue calculator 130 and furthermore, the user can be recommended to seek professional audiological evaluation in a step 578. This could be done by an in situ auditory or visual warning in step 580 by system 100. On the other hand, if system 100 is used in connection with a communications device such as a telephone or a personal digital assistant, an e-mail can be created in steps 574, 576; not only warning the user of potential damage, but notifying a health professional so that a follow up examination can be performed.

It should be noted that a change in the hearing metric (e.g., a hearing sensitivity curve) is measured by system 100. In response to the user's hearing metric, the recovery time constant tau is updated. For example, tau is lengthened if the change in the user's hearing metric indicates the user has "sensitive ears", i.e., if, following loud sound exposure, the user's hearing sensitivity takes longer than seven hours to return to the individual's normal. This modified tau can be used to calculate the sound pressure level dose, in particular in a restorative phase, to determine better overall effect of sound pressure level exposure.

By providing a monitoring and protective system which, in at least one mode, continuously monitors sound pressure level at the ear until a potentially harmful exposure has occurred, rather than only monitoring for a predetermined time as with noise dose monitors which monitor for work shifts, a more accurate predictor of harm to the ear is provided. By utilizing a method, which determines exposure in part as a function of effective quiet exposure as well as intense noise exposure, an enhanced model of potential risk is achieved. By providing a series of warning mechanisms and preventive measures as a function of the determined potentially harmful dosage levels ear damage is more likely to be prevented. By providing the system in an earpiece which substantially occludes the ear and making use of audio inputs at the lateral and medial portions of the ear canal (particularly with an occluding device between lateral and medial portions of the ear canal), a more accurate reading of noise level is provided and more control through a real time warning system is achievable.

It should be known that values for level change threshold, effective quiet time, and epoch were used above as examples. However, it should be noted that any values which when input and utilized in accordance with the methodologies above prevent permanent damage to the ear are within the scope of the invention and the invention should not be so limited to the specific examples above.

Further Exemplary Embodiments

Figure 8:
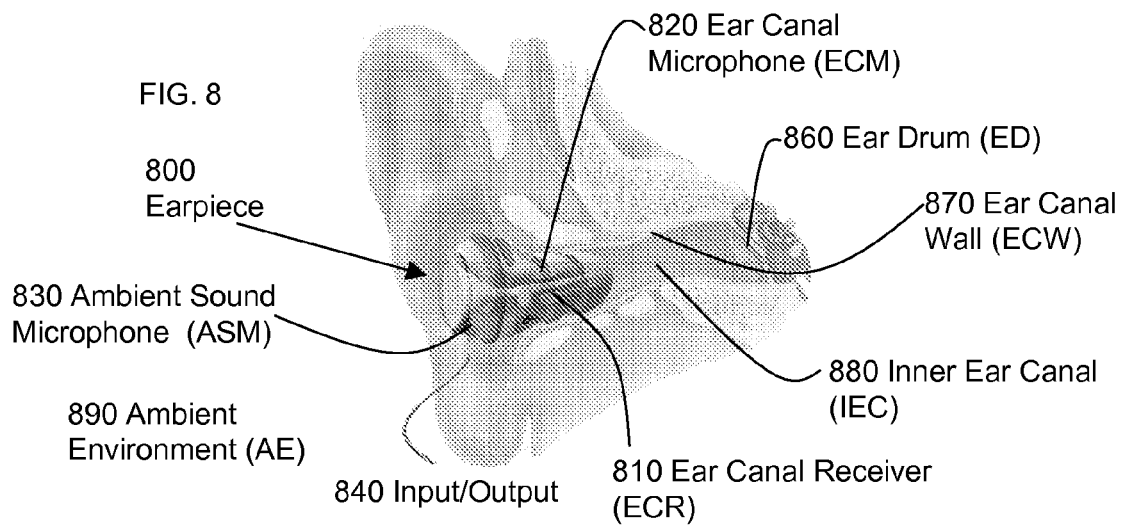
FIG. 8 illustrates the general configuration and terminology in accordance with descriptions of exemplary embodiments.

FIG. 8 illustrates the general configuration and some terminology in accordance with descriptions of exemplary embodiments. An earpiece 800 can be inserted into an ear canal separating the ambient environment (AE) 890 from an inner ear canal (IEC) 880 region, where a portion of the earpiece 800 touches a part of the ear canal wall (ECW) 870. The earpiece 800 can be designed to vary its distance from the eardrum (ED) 860. The earpiece 800 can have various elements, and the non-limiting example illustrated in FIG. 8, can include three sound producing or receiving elements coupled to input/output 840: an ambient sound microphone (ASM) 830 configured to sample the AE 890; an ear canal microphone (ECM) 820 configured to sample the IEC 880; and an ear canal receiver (ECR) 810 configured to acoustically emit into the IEC 880.

Figure 9A:
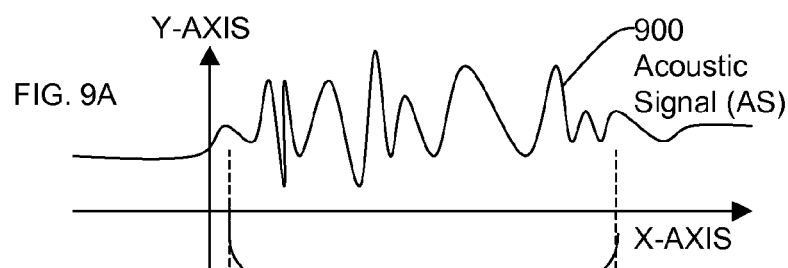
FIGS. 9A-9C illustrates an example of a temporal acoustic signal and its conversion into a spectral acoustic signature.
Figure 9B:
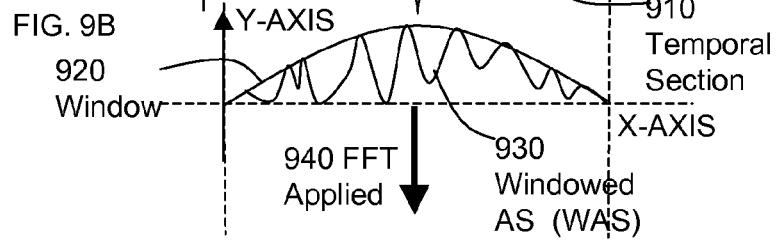
Figure 9C:
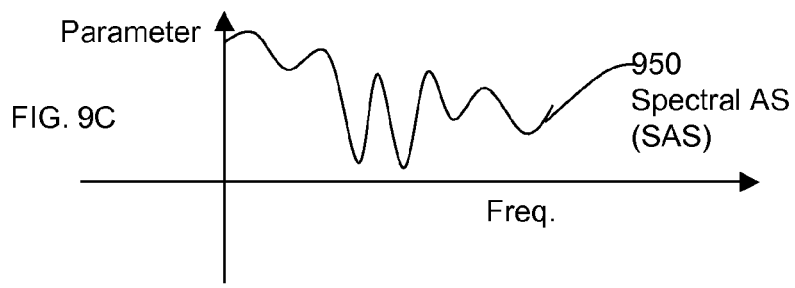

FIGS. 9A-9C illustrates an example of a temporal acoustic signal and its conversion into a spectral acoustic signature. FIG. 9A illustrates a temporal acoustic signal (AS) 900 on a generic X-Y coordinate system (e.g., Y can be amplitude in dB, and X can be time in sec). A section 910 of the AS 900 can be selected for further processing (e.g., for applying filtering treatments such as a FFT). For the non-limiting example of using a Fast Fourier Transform (FFT) on section 910, a window 920 can be applied to the section 910 to zero the ends of the data, creating a windowed acoustic signal (WAS) 930. An FFT can then be applied 940 to the WAS 930 to generate a spectral acoustic signal (SAS) 950, which is illustrated in FIG. 9C, where the Y-axis is a parameter (e.g., normalized power) and the X-axis is frequency (e.g., in Hz).

Figure 10:
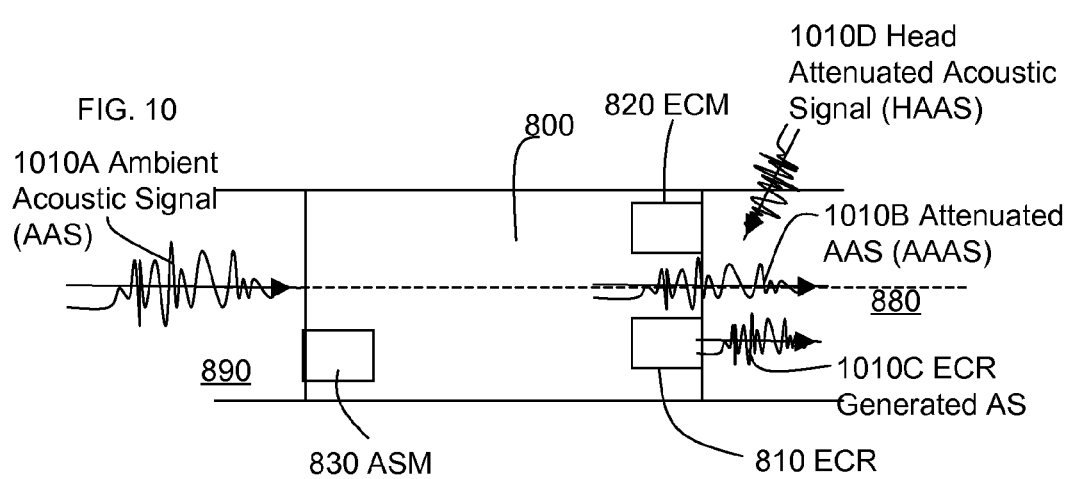
FIG. 10 illustrates a generalized version of an earpiece and some associated parts in an ear canal.

FIG. 10 illustrates a generalized version of an earpiece 800 and some associated parts (e.g., ASM 830, ECM 820, and ECR 810) in an ear canal. When inserted the earpiece 800 generally defines the two regions 890 and 880. Through the earpiece 800 there is some attenuation. For example an ambient acoustic signal (AAS) 1010A, will travel through the earpiece 800 and/or via bone conduction (not shown) and be attenuated forming an attenuated ambient acoustic signal (AAAS) 1010B. The AAAS 1010B then travels to the ED 860. The other additional acoustic signal 1010C (e.g., the ECR generated AS or ECRAS), which can travel to the eardrum 860, can be generated by the ECR 810. Thus the total AS imparting energy upon the ED 860 can be due to the AAAS 1010B (which can include a bone conduction part not in the IEC 880) and the ECRAS 1010C. Various exemplary embodiments can calculate SPL Dose due to the total imparting AS upon the ED 860, using various combinations of elements (e.g., parts) such as the ECR 810 (e.g., Knowles FG3629), the ECM 820 (e.g., Knowles FK3451), and the ASM 830 (e.g., Knowles FG3629). Note that ECM 820 can also measure head attenuated acoustic signals (HAAS) 1010D, which for example could originate from voice.

Figure 11:
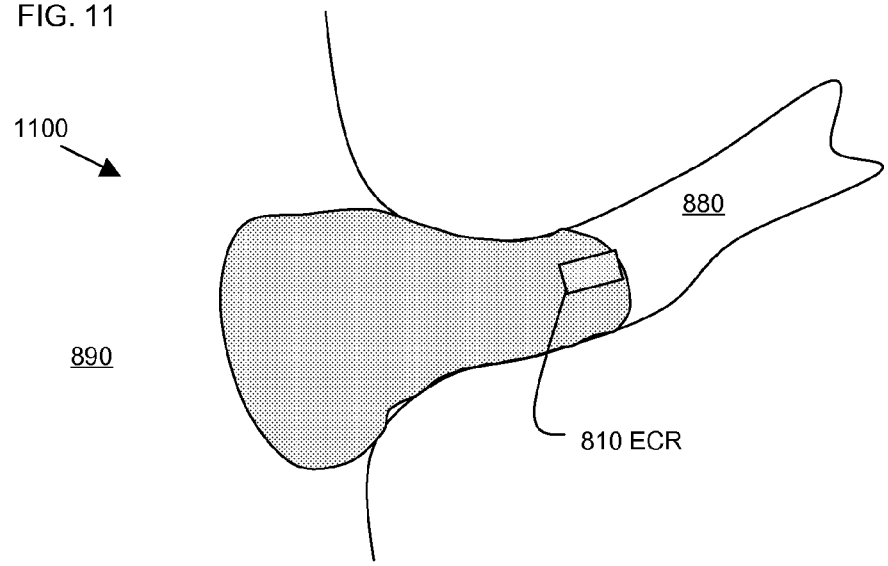
FIG. 11 illustrates an earpiece according to at least one exemplary embodiment.
Figure 12:
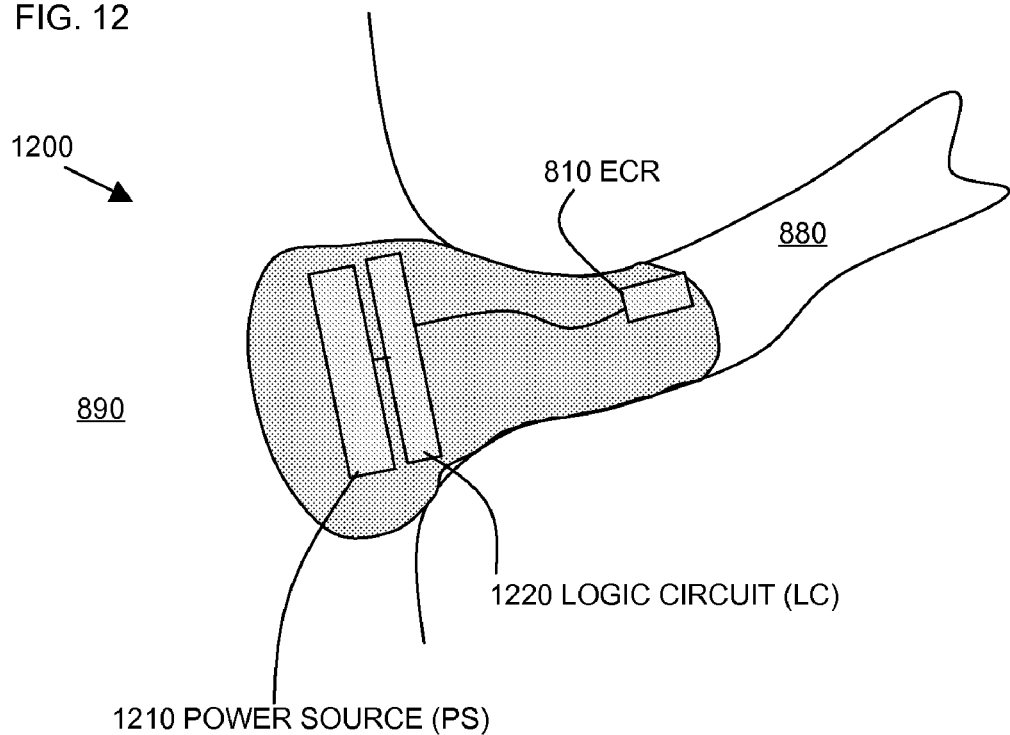
FIG. 12 illustrates a self contained version of an earpiece according to at least one exemplary embodiment.
Figure 13:
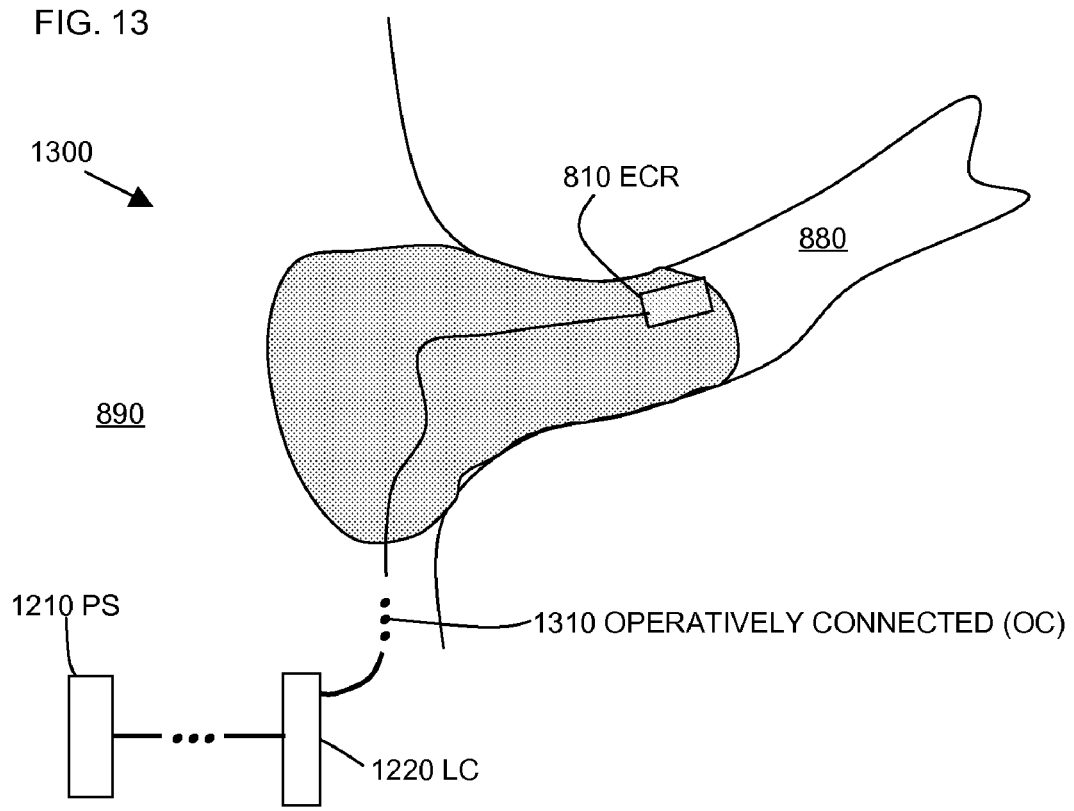
FIG. 13 illustrates an earpiece where parts are not contained in the earpiece directly according to at least one exemplary embodiment.

FIG. 11 illustrates an earpiece 1100 according to at least one exemplary embodiment including an ECR 810 and an ECM 820 (not shown). ECRAS 1010C generated by the ECR 810 can be predicted and used to predict an equivalent SPL Dose as discussed later. Note that additional elements (e.g., logic circuit(s) (LC), power source(s) (PS), can additionally be included in the earpiece 1100). For example FIG. 12 illustrates a self contained version of an earpiece 1200 according to at least one exemplary embodiment, including a power source (PS) 1210 (e.g., zinc-air battery (ZeniPower A675P), Li-ion battery), and a logic circuit (LC, e.g., Gennum Chip GA3280) 1220 in addition to ECR 810. Earpiece 1200 can also include a wireless module for wireless communications (not shown) or can be wired. Earpiece 1200 can also connect remotely to various parts (e.g., via a wired or wireless connection). For example FIG. 13 illustrates an earpiece 1300 where parts are not contained in the earpiece directly according to at least one exemplary embodiment. As illustrated the LC 1220 and PS 1210 are operatively connected (OC) 1310 (e.g., via a wire or wirelessly) to the earpiece 1300. For example earpiece 1300 can be an earbud that includes ECR 810, whose signals travel back and forth via a wire that is operatively connected via a wire to LC 1220, which in turn can be operatively connected to PS 1210. Note that ECR 810 can also be a dual purpose ECR/ECM, where when the receiver function (ECR mode) is not used the microphone function (ECM mode) can be used. For example U.S. Pat. No. 3,987,245 discusses a dual purpose transducer that can be used as a microphone and/or a receiver.

Figure 14A:
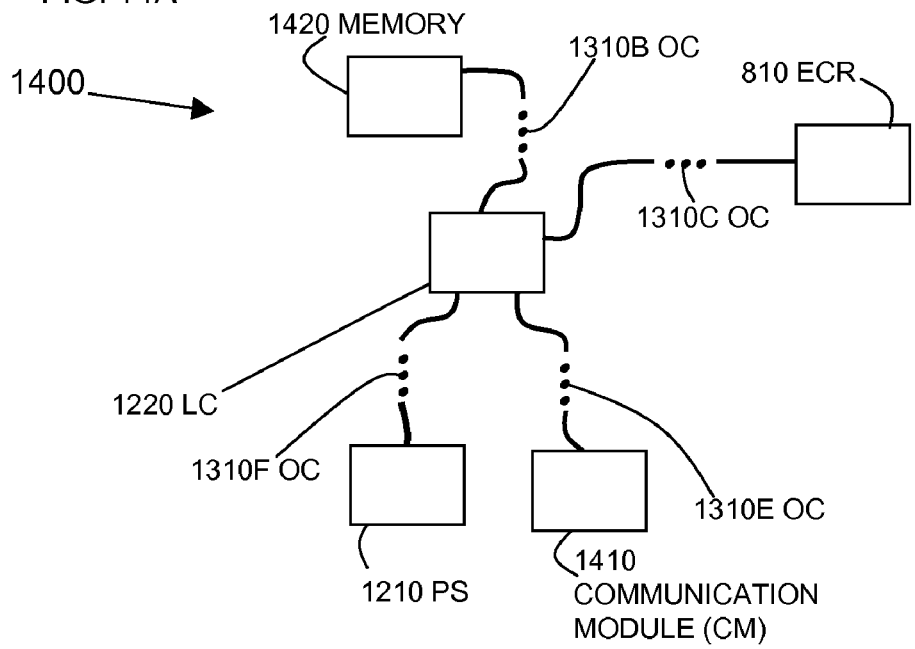
FIG. 14A illustrates a general configuration of some elements of an earpiece according to at least one exemplary embodiment.

FIG. 14A illustrates a general configuration of some elements either in or connected to an earpiece 1400 (e.g., via a wired or wireless connection) according to at least one exemplary embodiment. Illustrated is a logic circuit LC 1220 that is operatively connected 1310B to a readable memory 1420. LC 1220 can store and read data on the readable memory 1420 (e.g., RAM). LC 1220 can also be operatively connected 1310C to ECR 810, such that acoustic signals can be received by LC 1220 from ECR 810 and signals sent from LC 1220 to ECR 810, where ECR 810 is configured to direct acoustic energy toward the eardrum. LC 1220 can also be operatively connected 1310E (e.g., via wire or wireless) to a communication module 1410 (e.g., Bluetooth communication module). To power the various elements a power source 1210 PS can also be operatively connected 1310F to LC 1220 and to any other element.

Figure 14B:
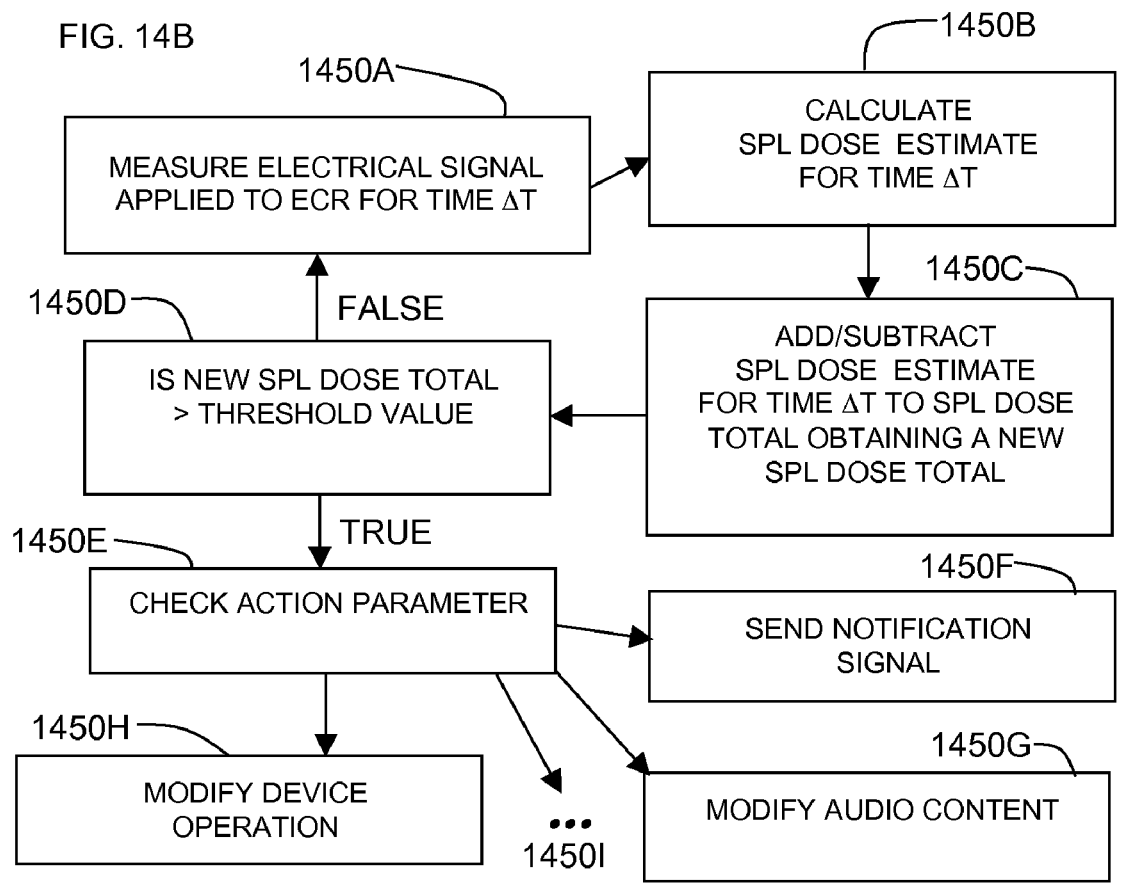
FIG. 14B illustrates a flow diagram of a method for SPL Dose calculation according to at least one exemplary embodiment.

FIG. 14B illustrates a flow diagram of a method for SPL Dose calculation according to at least one exemplary embodiment. A signal (e.g., intended audio playback content, or received voice from a phone) can be sent to LC 1220 to be sent to the ECR 810. The signal can be converted (e.g., using earpiece frequency response) to calculate the SPL(t) associated with the signal being sent to ECR 810. Thus the signal to the ECR 810 can be measured in step 1450A, an SPL measured for a chosen period of time. An SPL_Dose estimate is calculated as described above, in a step 1450B. The SPL_Dose estimate is added/subtracted to/from a running SPL Dose total to obtain a new SPL Dose total in a step 1450C. The new SPL Dose total is compared to a threshold value in a step 1450D. If the threshold value is exceeded the LC 1220 compares a check action parameter, which can be a user defined variable, to determine one or more actions to take in a step 1450E. For example if the action parameter is a certain value (e.g., 1) then the action can be to modify device operation in a step 1450H. For example, to shut down the device after a period of time (e.g., 5 seconds). Alternatively or cumulatively, if the action parameter is another value (e.g., 2), a notification signal can be sent (e.g., acoustic notice, for example a ringing) in a step 1450F, and/or if the action parameter is still another value (e.g., 3) the audio content can be modified (e.g., SPL output by ECR s reduced), in a step 1450G. Note other actions can be included, in a step 1450I, for example the NRR can be increased (e.g., if an inflatable system, the inflatable system can be expanded, or active noise cancellation could be activated).

Note that at least one exemplary embodiment can use an ECR 810 without dual functionality (e.g., where dual functionality is an ECR that can be a receiver and/or a microphone) and at least one further exemplary embodiment can be a dual function ECR/ECM. To measure the SPL for an ECR only mode (ECR mode) the same SPL Dose equations described above can be used for the SPL estimated as discussed with reference to FIG. 14B. Additionally the $SPL_{ECR}$ can be estimated by an ECR instrument response, e.g., a voltage to FFE dBA transfer function, which could be determined one of two ways: apply voltage to ECR 810 and follow the technique outlined in ISO 11904-2 (2002), using an acoustic manikin and/or apply voltage to ECR 810 and follow the technique outlined in ISO 11904-1 (2002), using probe microphone measurements in a human's ear canal; and/or about a 2 cc coupler could substitute for a human's ear canal.

Figure 14C:
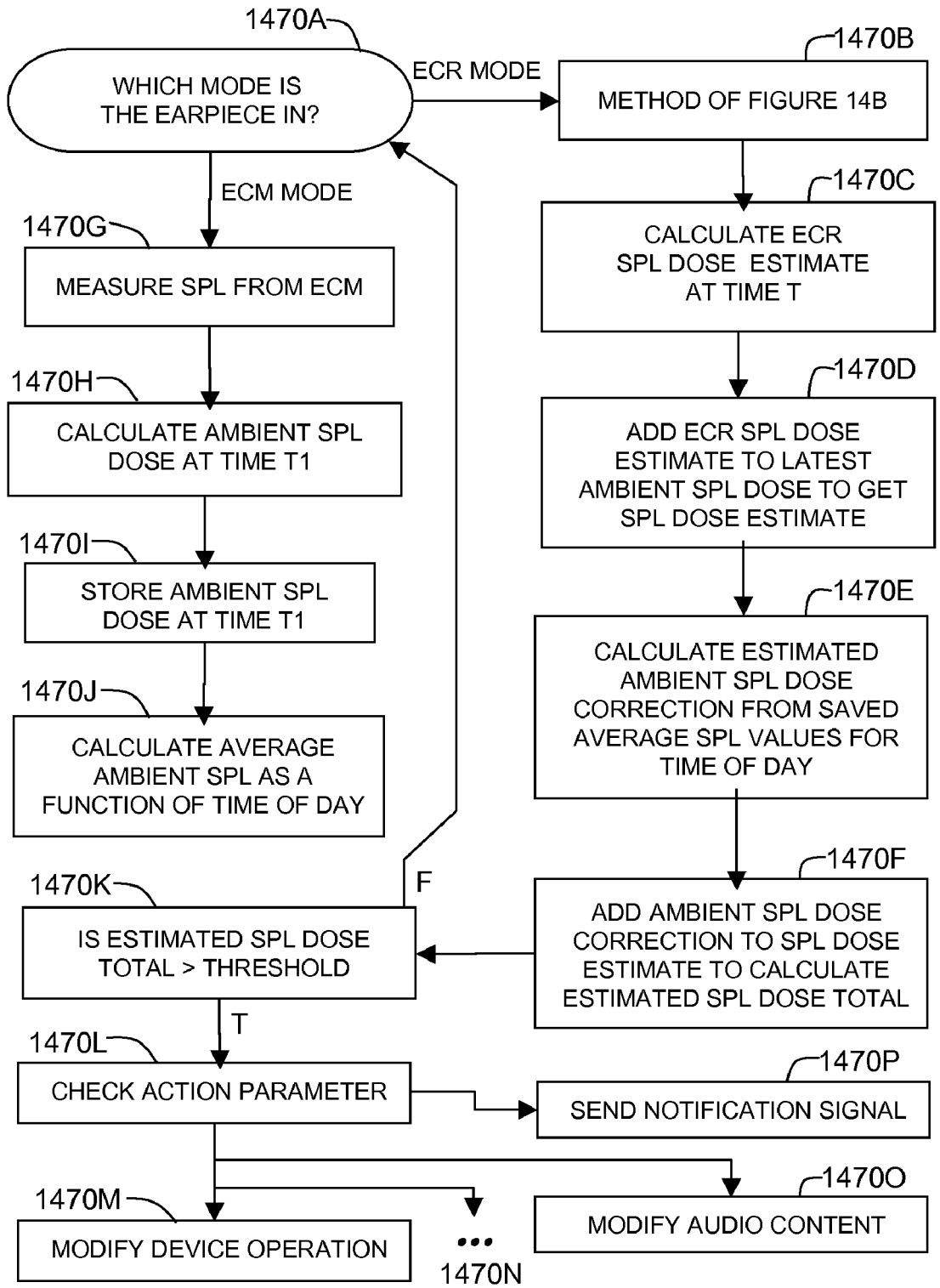
FIG. 14C illustrates a flow diagram of a method of SPL Dose calculation according to at least one exemplary embodiment.

FIG. 14C illustrates a flow diagram of a method of SPL Dose calculation according to at least one exemplary embodiment. In addition to an exemplary embodiment where only an ECR 810 is operating, a dual ECR/ECM can be used. Thus ECR 810 can be switched in such a case between an ECR mode, where audio signal is directed to the ECR 810 (e.g., audio playback (e.g., music, audio book, voice message), or voice conversation (e.g., voice from a phone, TV, computer)) or to an ECM mode, where ECR 810 acts as an ECM and samples environmental SPL. FIG. 14C illustrates a method in accordance with at least one exemplary embodiment and first comprises: determining which mode ECR 810 is in, ECR mode or ECM mode, in step 1470A. If ECR 810 is in the ECR mode the method as discussed with reference to FIG. 14B, in step 1470B, can be used to obtain an $SPL_{ECR}$ estimate, within the sample time "t" in a step 1470B, to either obtain $SPL\_Dose_{ECR}$ in a step 1470C, or save the value of $SPL_{ECR}$ to be added later to an SPL value for the environment, within sample time "t", to obtain a total SPL and then calculate a total SPL Dose in a step 1470D. Because in the ECR mode an ECM measurement is not made, the true environmental SPL value is not obtained, however several methods can be used to obtain a predicted sound pressure level (PSPL) for the environment during the ECR mode. One of these methods, others will be discussed with respect to FIGS. 15E and 17A, is to use the last $SPL_{ECM}$ value recorded, throughout the sample time "t" to obtain an $SPL\_Dose_{ECM}$ then add $SPL\_Dose_{ECR}$ to $SPL\_Dose_{ECM}$ to get SPL $Dose_{total}$. Alternatively, one can obtain $SPL_{total}=SPL_{ECR}+SPL_{ECM}$, then calculate SPL $Dose_{total}$ where $SPL_{total}$ can be used in "A" to determine if a recovery function is used for calculation of SPL $Dose_{total}$.

Additionally, ECM mode data can be saved as a function of day of the week and time of day, and used to correct any PSPL estimated that may occur at the same time and day in the future, which would correct any $SPL\_Dose_{ECM}$ obtained using PSPL in a step 1470E, and a new SPL $Dose_{total}$ can be calculated in a step 1470F. The new SPL Dose total can be compared to a threshold value in a step 1470K, and if the threshold value is exceeded the LC 1220 compares a check action parameter, which can be a user defined variable, to determine one or more actions to take in a step 1470L. For example if the action parameter is a certain value (e.g., A) then the action can be to modify device operation in a step 1470M, for example to shut down the device after a period of time (e.g., 10 seconds). Alternatively or cumulatively, if the action parameter is another value (e.g., B), a notification signal can be sent (e.g., acoustic notice, for example a notification voice recording) in a step 1470P, and/or if the action parameter is still another value (e.g., C) the audio content can be modified (e.g., SPL output by ECR can be reduced) in a step 1470O. Note other actions can be included in a step 1470N, for example the ECR emitted intensity can be reduced.

If ECR 810 is placed into ECM mode, then $SPL_{ECM}$ can be measured in ECM mode in a step 1470G, and an ambient SPL $Dose_{ECM}$ calculated during the sampling time "t1" in a step 1470H. Note the SPL $Dose_{ECM}$ calculated can be stored for future reference in a step 1470I and/or $SPL_{ECM}$ can be stored as a function of prediction variables (e.g., time of day, day of the week) in a step 1470J.

FIG. 14D illustrates a flow diagram of a method of SPL Dose calculation according to at least one exemplary embodiment. The method includes: calculating the SPL_Dose during the ECR mode for time increment "Δt" in a step 1480A. PSPL for the same time increment is calculated in a step 1480B. This can include using SPL data from ECM mode measurements saved in a database 1492. SPL_Dose for the ECM mode is calculated during the same time increment using PSPL. SPL_Dose total is calculated in a step 1480C. Note that SPL for the ECR mode and PSPL can be combined forming an SPL total and then SPL_Dose total is calculated in a step 1480D. SPL_Dose total is compared to a threshold value, for example the threshold value can be equivalent to a % of the remaining allowable SPL_Dose during the day (e.g. SPL_Dose is 90% allowable but with only 5% of the day remaining) in a step 1480E, and if the threshold value is exceeded the LC 1220 compares a check action parameter, which can be a user defined variable, to determine one or more actions to take in a step 1480F. For example if the action parameter is a certain value (e.g., MOD) then the action can be to modify device operation in a step 1480J, for example to shut down any ECR generated audio content. Alternatively or cumulatively, if the action parameter is another value (e.g., NOTF), a notification signal can be sent (e.g., acoustic notice, for example an acoustic earcon) in a step 1480G, and/or if the action parameter is still another value (e.g., AUDCON) the audio content can be modified (e.g., SPL output by ECR can be reduced) in a step 1480H. Note other actions can be included in an omnibus step 1480I, for example the ECR emitted intensity can be reduced.

FIGS. 15A-15E illustrate a method of switching between ECR and ECM modes in accordance with at least one exemplary embodiment. FIG. 15A illustrates a plot of $SPL_{ECR}$ versus time. At certain times, e.g. t1, $SPL_{ECR}$ falls below a selected floor (SF), e.g., threshold hearing SPL level at 1000 Hz, which could last to a time of t1+Δt1. During this time period a dual ECM/ECR mode capable ECR 810 could then monitor ambient SPL levels in an ECM mode. Thus in at least one exemplary embodiment when the SPL in the ECR mode drops below the SF a trigger signal (e.g., $sts_{ECM}$) can be sent to LC 1220 to switch to ECM mode for measuring ambient SPL (FIG. 15B). There can be a delay, $t_{delay}$, between when the SPL in the ECR mode drops below SF and when the signal $sts_{ECM}$ is received by LC 1220. Upon receiving $sts_{ECM}$ the dual ECR/ECM mode capacity ECR 810 can start monitoring $SPL_{ECM}$, FIG. 15D.

Thus there will be sections of time throughout the day where $SPL_{ECM}$ is measured (e.g., t1 to t1+Δt1, t2 to t2+Δt2, t3 to t3+Δt3, and t4 to t4+Δt4), these values can be saved and used later to fit a function of Predicted SPL (PSPL) for the particular day (e.g., $PSPL_{24}=A+Bt+Ct^2+Dt^3$, using a least squares fit to the measured data for that day to obtain coefficients A, B, C, D). In at least one exemplary embodiment $PSPL_{24}$ can be used at the end of the day to refine (e.g., replace, average with) the PSPL used during that day to update the SPL_Dose equation. Note that $PSPL_{24}$ can be saved in a database (i.e., the coefficients A, B, C, D) as a function of various variables (e.g., day of the week, holiday period, seasons) and refined (e.g., updated with more data) over time. Thus, in at least one exemplary embodiment, $PSPL_{24}$ for that day can be used to refine predicted $SPL_{ECM}$ (PSPL) during ECR mode, while the actual data $SPL_{ECM}$ is used when measured (e.g., FIG. 15E). Note since drive signals (e.g., audio playback signals, voice communication signals, alarm signals) sent (sometimes referred to herein as acoustic signals sent) to ECR 810 are known, then it will be known when to send a signal $sts_{ECR}$ to LC 1220 to switch back to ECR mode (FIG. 15C). Thus the total ambient SPL (FIG. 15E) before update with $PSPL_{24}$, will be a combination of calculated PSPL during ECR mode operations and actual measurements $SPL_{ECM}$.

There are multiple methods of calculating PSPL, and we will discuss five non-limiting examples in detail.

First Example of Calculating PSPL

The first non-limiting example for calculating PSPL uses averages of the preceding and following $SPL_{ECM}$ values with respect to the PSPL being predicted. Thus, with reference to FIGS. 15D and 15E, $PSPL_{ECM1}(t)$ can be estimated as:

$$PSPL_{ECM1}((t_1 + \Delta t_1) < t < t_2) = \frac{\left[\left(\frac{1}{\Delta t_1}\int_{t_1}^{t_1+\Delta t_1} SPL_{ECM1}(t)\,dt\right) + \left(\frac{1}{\Delta t_2}\int_{t_2}^{t_2+\Delta t_2} SPL_{ECM2}(t)\,dt\right)\right]}{2.0} \quad (15)$$

Thus, FIG. 15E illustrates PSPL estimates as straight lines (although of course other methods and techniques can be used that will not result in straight lines). These estimated PSPL can be later refined by use of $PSPL_{tupdate}$, where $PSPL_{tupdate}$, is an equation refined by the data over the tupdate period (e.g., $PSPL_{24}$, where tupdate is 24 hours in the non-limiting example previously discussed, note tupdate can be any period of time with enough data to solve the coefficients of the particular form of the equation). Note that the integrals can be replaced with summations, for example when manipulating digitized data.

Second Example of Calculating PSPL

A second non-limiting example of calculating PSPL uses weighted averages, where the $SPL_{ECM}$ data can be weighted according to several factors, for example the time increment during which measurements are made. A time incremented weighting can be expressed as:

$$PSPL_{ECM1}((t_1 + \Delta t_1) < t < t_2) = \quad (16)$$

$$\frac{\left[\frac{\Delta t_1}{\Delta t_1 + \Delta t_2}\left(\frac{1}{\Delta t_1}\int_{t_1}^{t_1+\Delta t_1} SPL_{ECM1}(t)\,dt\right) + \frac{\Delta t_2}{\Delta t_1 + \Delta t_2}\left(\frac{1}{\Delta t_2}\int_{t_2}^{t_2+\Delta t_2} SPL_{ECM2}(t)\,dt\right)\right]}{2.0}$$

Third Example of Calculating PSPL

A third non-limiting example is a linear model of the PSPL in time. For example, where in general PSPL is expressed as $PSPL(t)=X+Yt$. Using average values an example of a linear model can be expressed as:

$$PSPL_{ECM1}(t) = \frac{1}{\Delta t_1}\int_{t_1}^{t_1+\Delta t_1} SPL_{ECM1}(t)\,dt + \eta_{(t_1+\Delta t_1)\to t_2}(t)t \quad (17)$$

Where in this non-limiting example X is the average of the preceding $SPL_{ECM}$ values, and Y is $\eta$=constant, where $\eta$ can be expressed as:

$$\eta_{(t_1+\Delta t_1)\to t_2}(t) = \quad (18)$$

$$const. = \frac{1}{t_2 - (t_1 + \Delta t_1)}\left[\frac{1}{\Delta t_2}\left(\int_{t_2}^{t_2+\Delta t_2} SPL_{ECM2}(t)\,dt\right) - \frac{1}{\Delta t_1}\left(\int_{t_1}^{t_1+\Delta t_1} SPL_{ECM1}(t)\,dt\right)\right]$$

Fourth Example of Calculating PSPL

A fourth non-limiting example is a linear model of the PSPL in time. For example, where in general PSPL is expressed as $PSPL(t)=X+Yt$. Using preceding and trailing last values of $SPL_{ECM}$, where an example of a linear model can be expressed as:

$$PSPL_{ECM1}(t)=SPL_{ECM1}(t_1+\Delta t_1)+\eta_{(t_1+\Delta t_1)\to t_2}(t)t \quad (19)$$

Where in this non-limiting example X is the last of the preceding $SPL_{ECM}$ values, and Y is $\eta(t)$, where $\eta$ can be expressed as:

$$\eta_{(t_1+\Delta t_1)\to t_2}(t) = \frac{1}{t_2 - (t_1 + \Delta t_1)}[SPL_{EMC2}(t_2) - SPL_{ECM1}(t_1 + \Delta t_1)] \quad (20)$$

Fifth Example of Calculating PSPL

A fifth non-limiting example examines a non-linear model of PSPL in time. For example, where in general PSPL is expressed as $PSPL(t)=\alpha+\beta t+\delta t^2+\ldots$. In one method the actual values in the preceding and trailing sections of $SPL_{ECM}$ can be compared to the model PSPL results upon parameter (e.g., $\alpha$, $\beta$, $\delta$) choices in a least squares approach. Note in this case PSPL is modeled from $t_1$ to $t_2+\Delta t_2$. For example a model of PSPL can be solved via the expression:

$$PSPL_{ECM1}(t) \Rightarrow \alpha, \beta, \quad (21)$$

$$\delta \xrightarrow{minimize} \left(\int_{t_1}^{t_1+\Delta t_1}[PSPL_i(t) - SPL_{ECM1}(t)]^2\,dt + \int_{t_2}^{t_2+\Delta t_2}[PSPL_i(t) - SPL_{ECM2}(t)]^2\,dt\right)$$

Note to minimize one can take the derivative of the above equation and look for the inflection points as a function of i. Note in the above equation $PSPL_i$ can be expressed as:

$$PSPL_i(t)=\alpha_i+\beta_i t+\delta_i t^2+\ldots \quad (22)$$

where a value for $PSPL_i$ is obtained for "t" by selecting a guess ("ith" guess) for the parameters, then incrementing ("i+1") the parameters to get a new value for $PSPL_{i+1}$, the procedure of which is known by one of ordinary skill in the relevant arts.

Note that the above five examples of calculating PSPL are non-limiting examples and other methods can be used.

FIGS. 16A-16C illustrate the formation of SPL total from ECM and ECR values and estimated values (PSPL). For example FIG. 16A illustrates two SPL values in the interval 0 to $t_1$, $SPL_{ECR0}(t)$ and $PSPL_{ECM0}(t)$. Both of these values can be added to form $SPL_{total}(t)$ in the same interval from 0 to $t_1$ (FIG. 16B). As discussed the value of $SPL_{total}$ can be compared with PSL to determine whether one is in a SPL_Dose growth phase ($SPL_{total}>PSL$) or a recovery stage ($SRL_{total}<PSL$) (FIG. 16C). Note that the jumps in $SPL_{total}$ can result when no signal is sent to ECR 810 to emit acoustic energy to the eardrum. When SPL total is above PSL, SPL_Dose increases. Over the period of the day, SPL_Dose will increase or decrease. At least one exemplary embodiment adjusts the SPL_Dose after an update period (e.g., 24 hours). For example the data from actual measurements of $SPL_{ECM}$ (t) (e.g., during $t_1$ to $t_1+\Delta t_1$, during $t_2$ to $t_2+\Delta t_2$, during $t_3$ to $t_3+\Delta t_3$, and during $t_4$ to $t_4+\Delta t_4$) can be used to obtain a $PSPL_{update}$, for example using a method similar to the fifth PSPL calculating example discussed above. The values provided by the equation $PSPL_{update}(t)$ can be used in place of $PSPL_{ECM0}(t)$, $PSPL_{ECM1}(t)$, etc. . . . and the new values used to update SPL_Dose total. In at least one further exemplary embodiment, instead of replacing $PSPL_{ECM0}(t)$, $PSPL_{ECM1}(t)$, etc. . . . , the relevant values of $PSPL_{update}(t)$ can be combined (e.g., weighted average). For example FIGS. 17A-17C illustrate replacement of $PSPL_{ECM0}(t)$, $PSPL_{ECM1}(t)$, . . . values with relevant $PSPL_{day}(t)$ values, where the update time is 24 hours or a day. Thus FIG. 17A illustrates the estimated $SPL_{ECR}(t)$ values along with relevant $PSPL_{day}(t)$ values. Note that the actual measured values of $SPL_{ECM}(t)$ can be used instead of the $PSPL_{day}(t)$ values in the time increment (e.g., from $t_1$ to $t_1+\Delta t_1$). The final $SPL_{total-adjusted}(t)$ values can be obtained by combining $SPL_{ECR}(t)$ values along with relevant $PSPL_{day}(t)$ values, FIG. 17B, where $SPL_{total-adjusted}(t)$ can have different values than $SPL_{total-unadjusted}(t)=SPL_{total}(t)$ (FIG. 16C) as illustrated in FIG. 17C. As mentioned previously when $SPL_{total}>PSL$, SPL_Dose is in a growth stage, and when $SPL_{total}<PSL$, SPL_Dose is in a recovery stage, as illustrated in FIG. 17D.

Figure 18A:
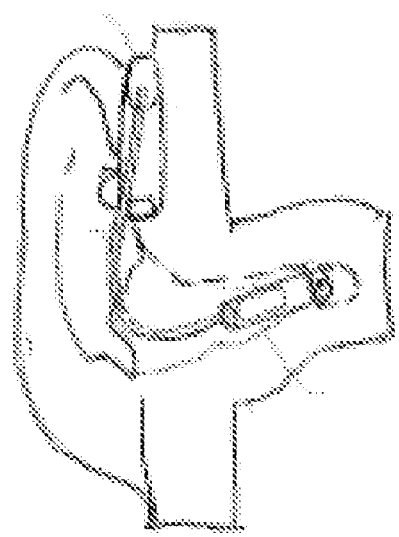
FIGS. 18A to 18N illustrate various non-limiting examples of earpieces that can use methods according to at least one exemplary embodiment.
Figure 18B:
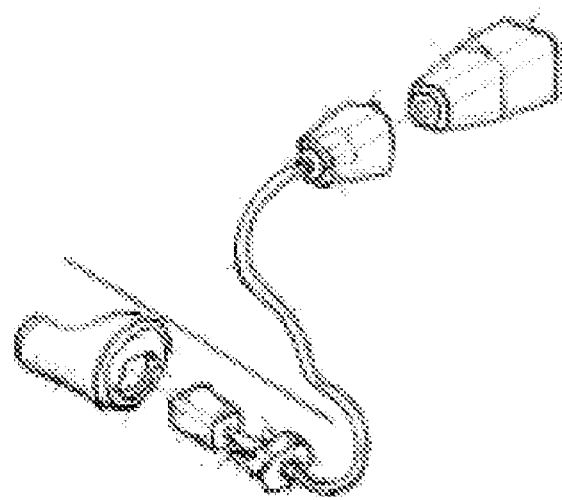
Figure 18C:
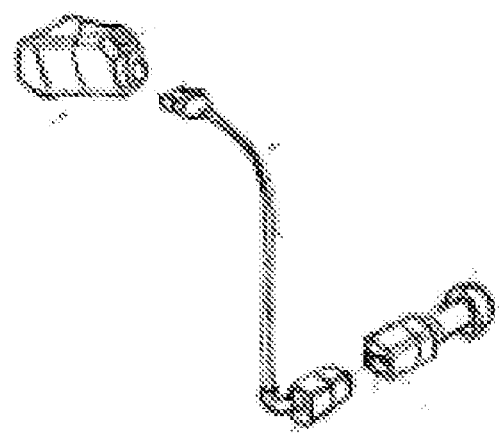
Figure 18D:
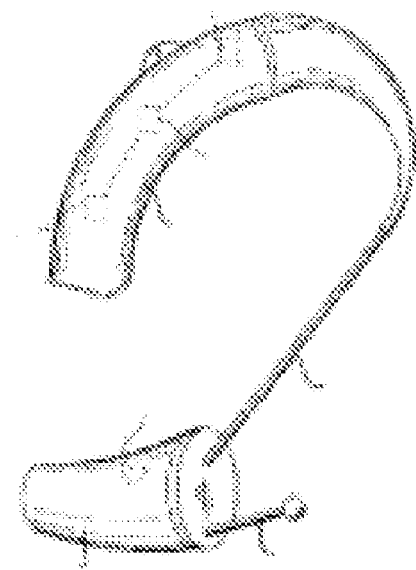
Figure 18E:
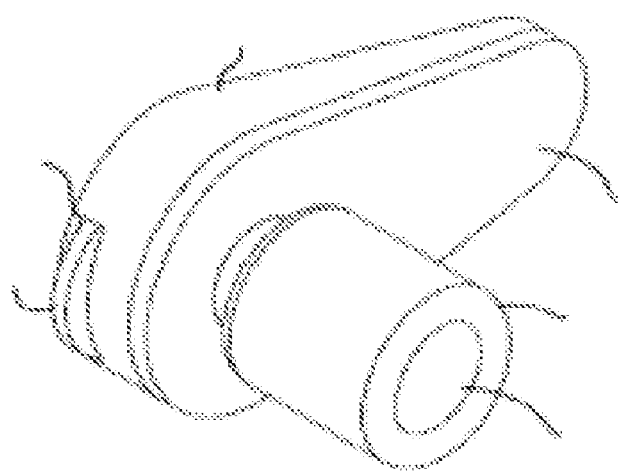
Figure 18F:
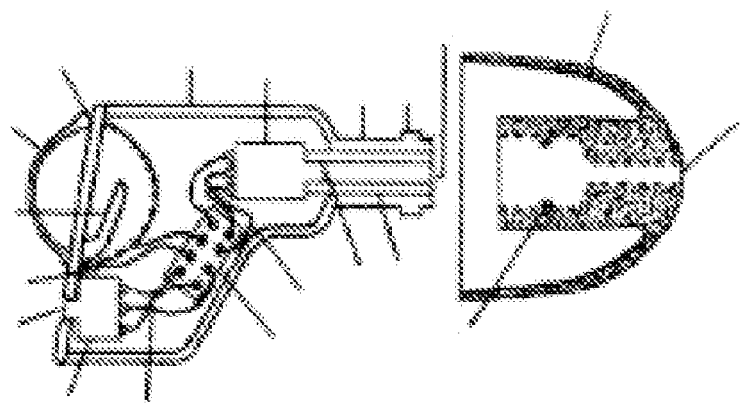
Figure 18G:
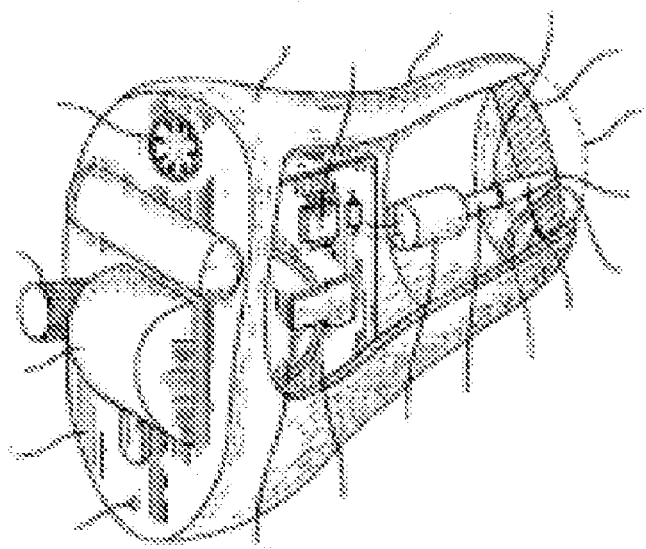
Figure 18H:
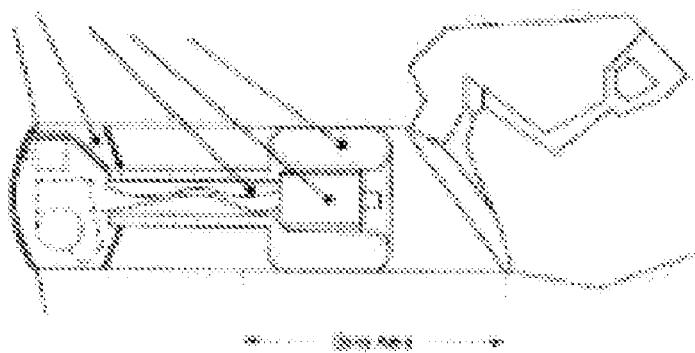
Figure 18I:
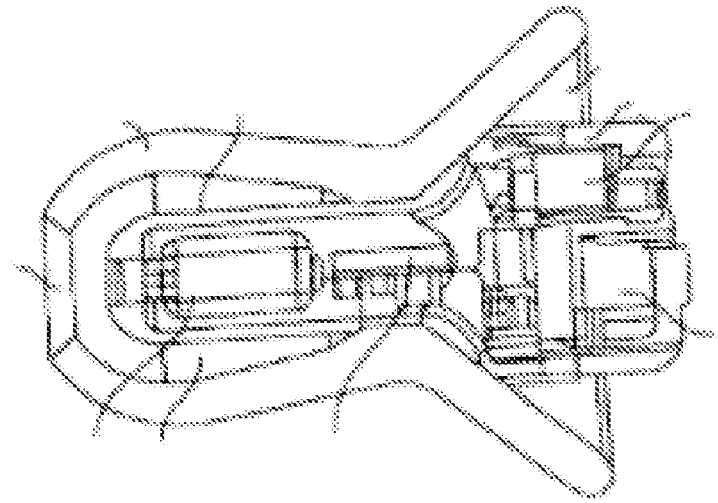
Figure 18J:
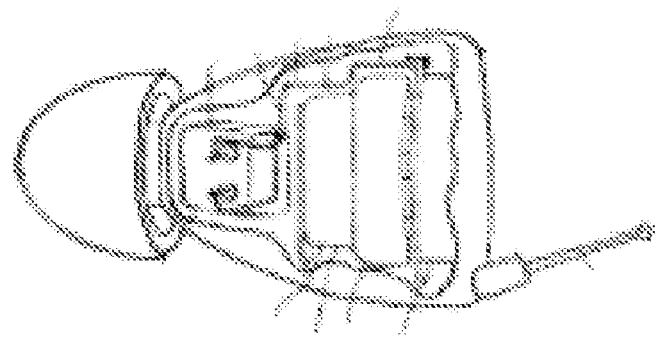
Figure 18K:
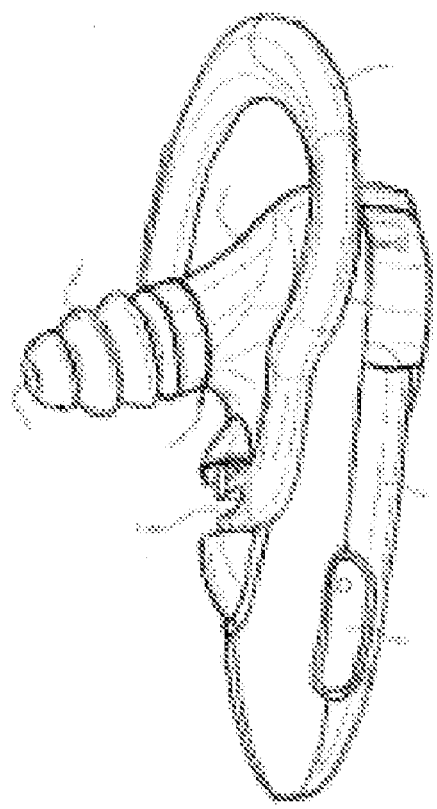
Figure 18L:
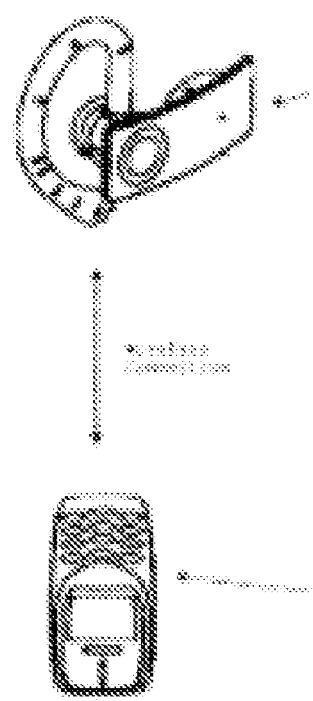
Figure 18M:
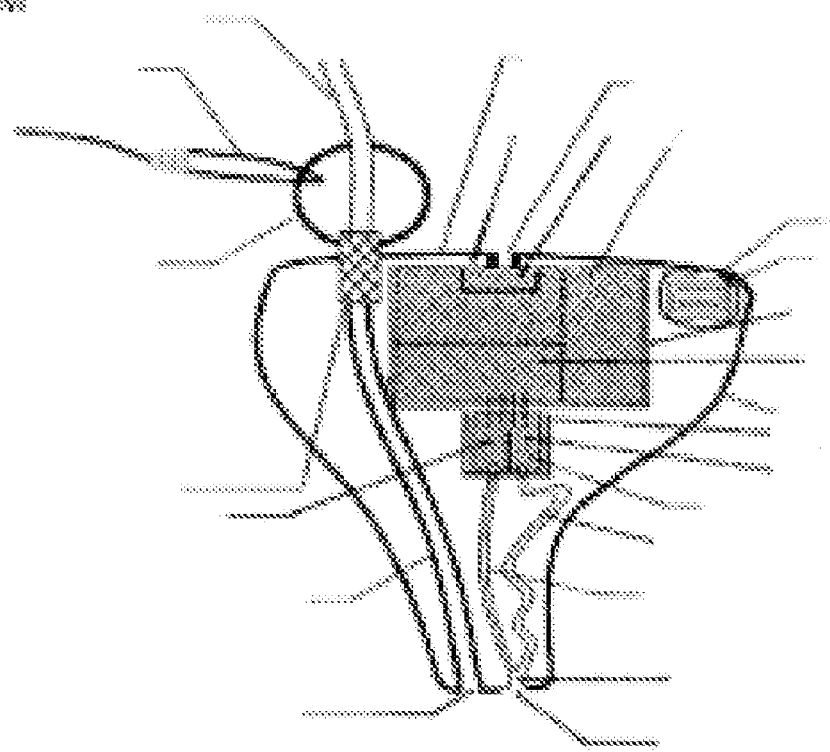
Figure 18N:
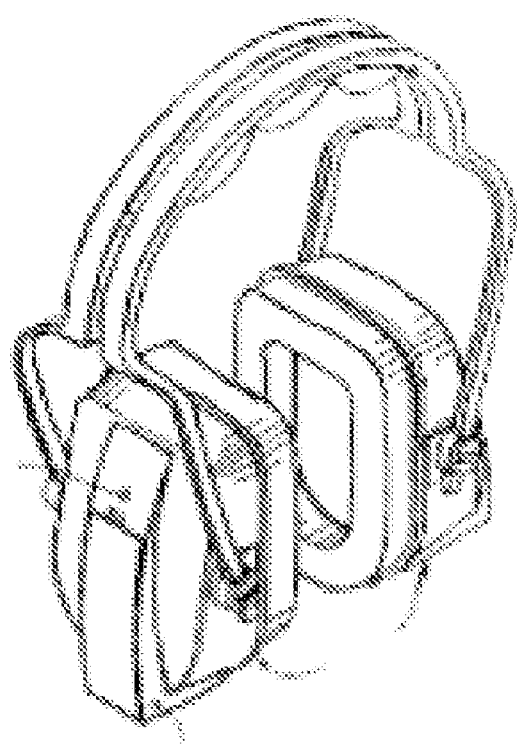

Exemplary embodiments of the present invention can be used in many platforms that direct and/or attenuate acoustic energy in the ear canal. FIGS. 18A to 18N illustrate various non-limiting examples of earpieces that can use methods according to at least one exemplary embodiment, when the various earpieces have an ECR 810 that is solely an ECR or have an ECR 810 that has dual ECR/ECM modes.

Figure 19:
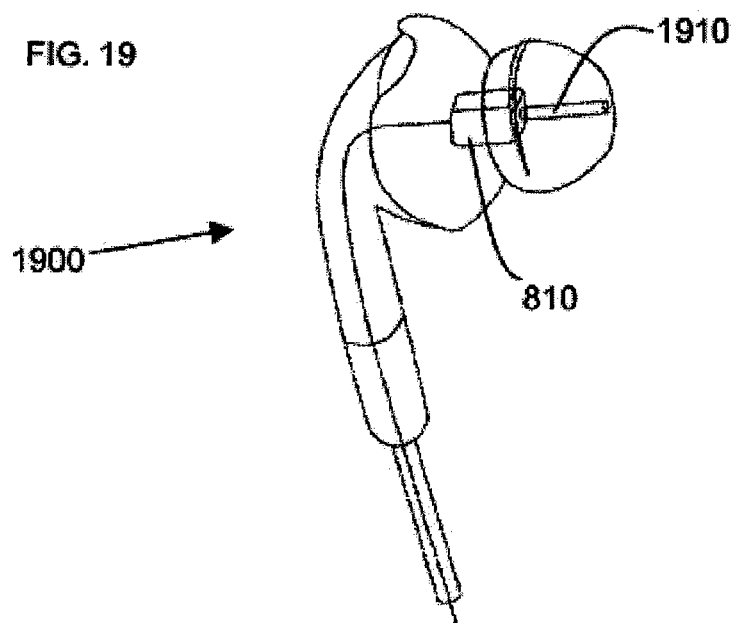
FIG. 19 illustrates a line diagram of an earpiece (e.g., earbud) that can use methods according to at least one exemplary embodiment.
Figure 20:
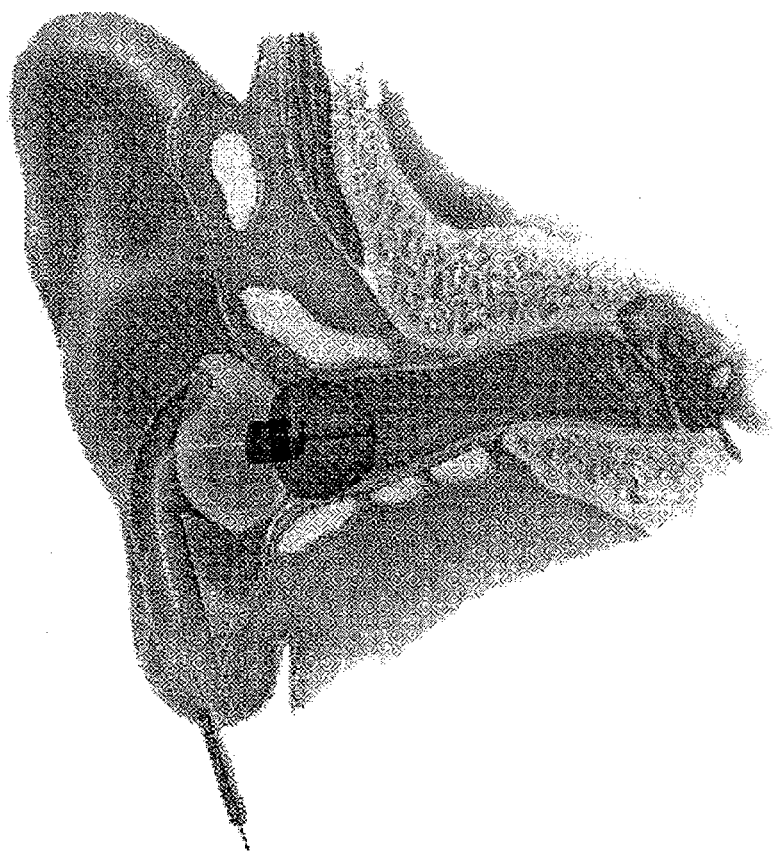
FIG. 20 illustrates the earpiece of FIG. 19 fitted in an ear.

FIG. 19 illustrates a line diagram of an earpiece 1900 (e.g., having earbud 1910) that can use methods according to at least one exemplary embodiment and FIG. 20 illustrates the earpiece of FIG. 19 fitted in an ear canal. Earbuds 1910 can be used with many devices such as audio playback devices, PDAs, phones, and other acoustic management devices. The software to implement exemplary embodiments can reside in the earpiece (e.g., hearing aid) or can reside in the acoustic management systems (e.g., iPod™, Blackberry™, and other acoustic management devices as known by one of ordinary skill in the relevant arts).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, although specific numbers may be quoted in the claims, it is intended that a number close to the one stated is also within the intended scope, i.e., any stated number (e.g., 80 dB) should be interpreted to be "about" the value of the stated number (e.g., about 80 dB). Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A method of operating an audio device configured to be inserted in an ear canal, the method comprising:
    measuring sound pressure levels (SPLs) for at least one electrical drive signal directed to an ear canal receiver (ECR) during a time period $\Delta t$ having a plurality of samples;
    determining a SPL dose of the at least one electrical drive signal during the time period $\Delta t$ using the measured sound pressure levels;
    simultaneously estimating an ambient SPL dose within the ear canal during the time period $\Delta t$;
    calculating a total SPL dose of the audio device using the SPL dose of the at least one electrical drive signal and the estimated ambient SPL dose; and
    performing an action by the audio device when the total SPL dose is greater than a predetermined threshold.

2. The method according to claim 1, further including:
    comparing the measured sound pressure levels for the at least one electrical drive signal to a permissible sound level (PSL), and if the measured sound pressure levels are less than the PSL within an error margin, then the step of determining the SPL dose uses a recovery function to generate the SPL dose during the time period $\Delta t$.

3. The method according to claim 2, where the error margin is zero.

4. The method according to claim 1, further comprising:
    reading an action parameter from a readable memory when the total SPL dose is greater than the predetermined threshold.

5. The method according to claim 1, where the action includes at least one of modifying an operation of the audio device, modifying the at least one electrical drive signal directed to the ECR, and sending an acoustic notification signal to a user.

* * * * *